US009365874B2

(12) United States Patent
Burk et al.

(10) Patent No.: US 9,365,874 B2
(45) Date of Patent: *Jun. 14, 2016

(54) METHODS FOR SYNTHESIS OF OLEFINS AND DERIVATIVES

(71) Applicant: Genomatica, Inc., San Diego, CA (US)

(72) Inventors: Mark J. Burk, San Diego, CA (US); Priti Pharkya, San Diego, CA (US); Stephen J. Van Dien, Encinitas, CA (US); Anthony P. Burgard, Bellefonte, PA (US); Christophe H. Schilling, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/887,140

(22) Filed: May 3, 2013

(65) Prior Publication Data

US 2013/0316426 A1 Nov. 28, 2013

Related U.S. Application Data

(63) Continuation of application No. 13/219,423, filed on Aug. 26, 2011, now Pat. No. 8,455,683, which is a continuation of application No. 12/188,582, filed on Aug. 8, 2008, now Pat. No. 8,026,386.

(60) Provisional application No. 60/955,321, filed on Aug. 10, 2007.

(51) Int. Cl.
| | |
|---|---|
| *C12P 7/40* | (2006.01) |
| *C12P 7/42* | (2006.01) |
| *C12P 7/62* | (2006.01) |
| *C12N 1/21* | (2006.01) |
| *C07C 51/353* | (2006.01) |
| *C07C 57/04* | (2006.01) |
| *C07C 67/08* | (2006.01) |
| *C07C 67/333* | (2006.01) |
| *C12P 7/46* | (2006.01) |
| *C07C 51/38* | (2006.01) |
| *C07C 67/32* | (2006.01) |

(52) U.S. Cl.
CPC ............... *C12P 7/40* (2013.01); *C07C 51/353* (2013.01); *C07C 51/38* (2013.01); *C07C 57/04* (2013.01); *C07C 67/08* (2013.01); *C07C 67/32* (2013.01); *C07C 67/333* (2013.01); *C12P 7/46* (2013.01); *C12P 7/62* (2013.01)

(58) Field of Classification Search
None
See application file for complete search history.

(56) References Cited

U.S. PATENT DOCUMENTS

| | | | |
|---|---|---|---|
| 2,894,982 A * | 7/1959 | Greenberg et al. | ........... 560/204 |
| 4,082,788 A | 4/1978 | Mims | |
| 5,869,301 A | 2/1999 | Nghiem et al. | |
| 6,500,975 B1 | 12/2002 | Schwab et al. | |
| 7,127,379 B2 | 10/2006 | Palsson et al. | |
| 7,799,545 B2 | 9/2010 | Burgard et al. | |
| 7,803,589 B2 | 9/2010 | Burk et al. | |
| 7,947,483 B2 | 5/2011 | Burgard et al. | |
| 2002/0012939 A1 | 1/2002 | Palsson | |
| 2002/0040123 A1 | 4/2002 | Patil et al. | |
| 2002/0168654 A1 | 11/2002 | Maranas et al. | |
| 2003/0059792 A1 | 3/2003 | Palsson et al. | |
| 2003/0224363 A1 | 12/2003 | Park et al. | |
| 2003/0233218 A1 | 12/2003 | Schilling et al. | |
| 2004/0009466 A1 | 1/2004 | Maranas et al. | |
| 2004/0029149 A1 | 2/2004 | Palsson et al. | |
| 2004/0072723 A1 | 4/2004 | Palsson et al. | |
| 2006/0046288 A1 * | 3/2006 | Ka-Yiu et al. | ................ 435/145 |
| 2009/0023182 A1 * | 1/2009 | Schilling | ......................... 435/42 |

FOREIGN PATENT DOCUMENTS

| | | |
|---|---|---|
| EP | 1075482 A1 | 2/2001 |
| EP | 1647594 A1 | 4/2006 |
| WO | 02055995 A2 | 7/2002 |
| WO | 03106998 A1 | 12/2003 |
| WO | 2004062763 A2 | 7/2004 |
| WO | 2006031424 A2 | 3/2006 |
| WO | 2008024023 A2 | 2/2008 |

OTHER PUBLICATIONS

Claim set for U.S. Appl. No. 13/887,140 submitted on Aug. 27, 2013 having duplicate claim numbers.*
Appling et al., Regulation of expression of the ADE3 gene for yeast C1-tetrahydrofolate synthase, a trifunctional enzyme involved in one-carbon metabolism, J. Biol. Chem., 1985, 260, 1248-56.*
Zhao et al., Global metabolic response of *Escherichia coli* to gnd or zwf gene-knockout, based on 13C-labeling experiments and the measurement of enzyme activities, Appl. Microbiol. Biotechnol., 2004, 64, 91-98.*
Vidal et al., Development of an antibiotic-free plasmid selection system based on glycine auxotrophy for recombinant protein overproduction in *Escherichia coli*, Microbial Cell Factories, 2006, 5 (Suppl I), P85.*
Song et al., Metabolic engineering of *Escherichia coli* for the production of fumaric acid, Biotech. Bioeng., 2013, 110, 2025-34.*
Du, Jianxin et al. "Fumarc Acid Production in Airlift Loop Reactor Porous Sparger," Applied Biochemistry and Biotechnology, (1997), pp. 541-556, 63-65.
Aldrich Catalog, Sigma-Aldrich Company, (2002), p. 481, Milwaukee, WI.

(Continued)

*Primary Examiner* — Robert Mondesi
*Assistant Examiner* — Todd M Epstein
(74) *Attorney, Agent, or Firm* — Kagan Binder, PLLC

(57) ABSTRACT

The invention provides a method of producing acrylic acid. The method includes contacting fumaric acid with a sufficient amount of ethylene in the presence of a cross-metathesis transformation catalyst to produce about two moles of acrylic acid per mole of fumaric acid. Also provided is an acrylate ester. The method includes contacting fumarate diester with a sufficient amount of ethylene in the presence of a cross-metathesis transformation catalyst to produce about two moles of acrylate ester per mole of fumarate diester. An integrated process for process for producing acrylic acid or acrylate ester is provided which couples bioproduction of fumaric acid with metathesis transformation. An acrylic acid and an acrylate ester production also is provided.

15 Claims, 4 Drawing Sheets

(56) References Cited

OTHER PUBLICATIONS

Bai et al., "Lewis-acid assisted cross metathesis of acrylonitrile with functionalized olefins catalyzed by phosphine-free ruthenium carbine complex," Org. Biomol. Chem., (2005), pp. 4139-4142, 3(22).

Burgard et al., "Optknock: a bilevel programming framework for identifying gene knockout strategies for microbial strain optimization," Biotechnol. Bioeng., (2003), pp. 647-657, 84(6).

Chatterjee et al., "A general model for selectively in olefin cross methathesis," J. Am Chem. Soc. (2003), 125(37), pp. 11360-11370.

Choi et al., "Olefin Metathesis Involving Ruthenium Enoic Carbene Complexes," Journal of the American Chemical Society, (2001), pp. 10417-10418, 123.

Couturier et al., "A Cyclometalated Aryloxy(chloro)neopentylidenetungsten Complex: A Highly Active and Stereoselective Catalyst for the Metathesis of cis- and trans-2-Pentene, Norbornene, 1-Methyl-norbornene, and Ethyl Oleate," Angew. Chem Int. Ed. Engl., (1992), pp. 628-631, 31(5).

Database Reaxys [Online] Elsevier Properties SA; RX-ID Nos. 715357 and 5957085; Volmar: Comptes Rendus Hebomadaires Des Seances De L'Academie Des Sciences, (1925), p. 467, 181 (document printed Apr. 11, 2011).

Dias et al., "Well-Defined Ruthenium Olefin Metathesis Catalyst: Mechanism and Activity," J. Am. Chem. Soc., (1997), pp. 3887-3897, 119(17).

Edwards and Palsson, "The *Escherichia coli* MG1655 in silico Metabolic Genotype: Its Definition, Characteristics, and Capabilities," Proc. Natl. Acad. Sci. USA, (2000), pp. 5528-5533, 97(10).

Edwards et al., "In Silico Predictions of *Escherichia coli* metabolic capabilities are Consistent with Experimental Data," Nat. Biotechnol. (2001), pp. 125-130, 19(2).

Edwards et al., "Metabolic modelling of microbes: the flux-balance approach," Environ. Microbiol., (2002), pp. 133-140, 4(3).

Fomine et al., "Cross-methathesis of dimethyl maleate and ethylene catalyzed by second generation ruthenium carbene compleses: B3LYP and MPW1K comparison study," J. Org. Chem., (2006), pp. 5189-5196, 691.

Frost, "Redefining chemical manufacture. Replacing petroleum with plant-derived feedstocks," Ind. Biotechnol., (2005), pp. 23-24, 1(1).

Gibson et al., "Cross methathesis of the amino acid homoallylglycine," Chem. Commun., (1997), pp. 1107-1108.

Grubbs, "Olefin Meethathesis," Tetrahedron, (2004), pp. 7117-7140, 60.

Hayes et al., "The Biofine Process: Production of Levulinic Acid, Furfural and Formic Acid from Lignocellulosic Feedstocks," In Biorefineries: Industrial Proceses and Products, Wiley, (2006), pp. 139-164, Weinheim, Germany.

Howard et al., "Titanium Metallacarbene-Metallacylobutane Reactions: Stepwise Metathesis," J. Am. Chem. Soc., (1980), pp. 6876-6878, 102.

Kaclikova et al., "Fumaric acid overproduction in yeast mutants deficient in fumarase," FEMS Microbiol. Lett., (1992), pp. 101-106, 91(2).

Kenealy et al., "Biochemical Aspects of Fumaric Acid Accumulation by Rhizopus arrhizus," Appl. Environ. Microbiol. (1986), pp. 128-133, 52.

Kress et al., "First direct observation of the simultaneous presence and of the interconversion of chain-propagating metal-carbene and metallacyclobutane complexes in a catalytic olefin metathesis reaction: the ring-opening polymerization of norbornene," J. Am. Chem. Soc. (1987), pp. 899-901, 109(3).

Kress et al., "Tungsten(VI) and molybdenumVI oxo-alkyl species. Their role in the metathesis of olefins," J. Chem. Soc., Chem. Commun., (1980), pp. 431-432.

Lloyd-Jones et al., "Rate Enhancement by Ethylene in the Ru-Catalyzed Ring-Closing Metathesis of Enynes: Evidence for an "Enethen-Yne" Pathway that Diverts through a Second Catalytic Cycle," Angew Chem Int Ed., (2005), pp. 7442-7447, 44(45).

Lynn et al., "Living Ring-Opening Metathesis Polymerization in Aqueous Media Catalyzed by Well-Defined Ruthenium Carbene Complexes," J. Am. Chem. Soc., (1996), pp. 784-790, 118(4).

Lynn et al., "Living Ring-Opening Metathesis Polymerization in Water," J. Am. Chem. Soc., (1998), pp. 1627-1628, 120(7).

Pine et al., "Titanium-Mediated Methylene-Transfer Reactions. Direct Conversion of Esters in to Vinyl Ethers," J. Am. Chem. Soc., (1980), pp. 3270-3272, 102.

Roa Engel et al., "Fumaric acid production by fermentation," Appl. Microbiol Biotechnol., (2008), pp. 379-389, 78(3).

Schilling et al., "Combining Pathway Analysis with Flux Balance Analysis for the Comprehensive Study of Metabolic Systems," Biotechnol. Bioeng., (2000), pp. 286-306, 71(4).

Schilling et al., "Theory for the Systematic Definition of Metabolic Pathways and Their Use in Interpreting Metabolic Function from a Pathway-Oriented Perspective," J. Theor. Biol., (2000), pp. 229-248, 203(3).

Schilling et al., "Toward Metabolic Phenomics: Analysis of Genomic Data Using Flux Balances," Biotechnol. Prog. (1999), pp. 288-295, 15(3).

Schrock et al., "Preparation and Reactivity of Several Alkylidene Complexes of the Type W(CHR')N—2, 6-C6H3-i-Pr2)(OR)2 and Related Tungstacyclobutane complexes. Controlling Metathesis Activity through the Choice of Alkoxide Ligand," J. Am. Chem. Soc., (1988), pp. 1423-1435, 110.

Solomons, Organic Chemistry, 5th edition, (1992), pp. 778-780, John Wiley & Sons, Inc., New York.

Straathof et al., "Feasibility of acrylic acid production by fermentation," Appl. Microbiol. Biotechnol., (2005), pp. 727-734, 67.

Tebbe et al., "Titanium-Catalyzed Olefin Metathesis," J. Am. Chem. Soc., (1979), pp. 5074-5075, 101(17).

Department of Energy, "Top value added chemicals from biomass. Volume I—Results of Screening for Potential Candidates from Sugars and Synthesis Gas," Biomass, Aug. 2004.

Varma and Palsson, "Metabolic Flux Balancing: Basic Concepts, Scientific and Practical Use," Biotechnology, (1994), pp. 994-998, 12.

Wang et al., "Bioconversion of fumaric acid to succinic acid by recombinant *E. coli*," App. Biochem. Biotechnol. (1998), pp. 919-928, 70-72.

Wengrovious et al., "Tungsten-Oxo Alkylidene Complexes as Olefin Metathesis Catalysts and the Crystal Structure of W(O)(CHCMe3)(PTt3)Cl21," J. Am. Chem. Soc., (1980), 515-4516, 102(45).

Willke and Vorlop, "Industrial bioconversion of renewable resources as an alternative to conventional chemistry," Appl. Microbiol. Biotechnol., (2004), pp. 131-142, 66(2).

\* cited by examiner

METHODS FOR SYNTHESIS OF OLEFINS AND DERIVATIVES

CROSS REFERENCE TO RELATED APPLICATIONS

This application is a continuation of U.S. patent application Ser. No. 13/219,423, filed Aug. 26, 2011, pending, which is a continuation of U.S. patent application Ser. No. 12/188,582, filed Aug. 8, 2008, now U.S. Pat. No. 8,026,386, issued Sep. 27, 2011, which claims the benefit of U.S. Provisional Application No. 60/955,321, filed Aug. 10, 2007, which are incorporated herein by reference in their entireties

STATEMENT OF FEDERALLY SPONSORED RESEARCH

This invention was made with government support under grant number DE-FG02-06ER84536 and DE-FG02-07ER84865 awarded by the Department of Energy. The United States Government has certain rights in this invention.

BACKGROUND OF THE INVENTION

This invention relates generally to the production of commodity and specialty chemicals and, more specifically to an integrated bioprocess for producing acrylic acid and acrylate esters.

Acrylic acid and acrylate esters are large volume petrochemical products. For example, acrylic acid is a commodity monomer intermediate used for the production of polymeric materials such polyacrylic acid, which is a major component of superabsorbant diapers. Acrylic acid also is used for the production of acrylate esters, which are utilized in water-soluble latex coatings, adhesives and inks. Acrylic acid and acrylate esters are manufactured by petrochemical processes such as oxidation of propylene, followed by esterification with alcohols such as methanol, butanol, and 2-ethylhexanol. These chemical products are manufactured at total volumes exceeding 10 billion lb/year and represent a market of over $10 B in sales. The annual growth for these markets is estimated to be 4-5% globally.

Chemicals manufactured from petroleum feedstocks suffer the burden of high and volatile prices, insecure foreign supply chains, and declining reserves (Frost, J. W., Redefining chemical manufacture. *Ind. Biotechnol.* 1:23-24 (2005)). Therefore, a method of producing large volume chemicals or their intermediates by alternative means that reduce petroleum-based processes and also use less energy- and capital-intensive processes would be beneficial. The ability to generate chemical compounds based on biological processes could provide one such alternative means. However, complete biosynthesis of a chemical compound is not always available, and in some instances, toxic to the host organism.

Chemical manufacture based on low cost renewable resources is another alternative for chemical manufacture as a possible displacement of petroleum-based raw materials such as propylene or butane. However, in order for such resources to replace current manufacturing methods new chemical or biosynthetic processes need to be developed for each resource and/or target chemical.

Thus, there exists a need for compositions and methods that reduce the use for petroleum-based synthesis of acrylic acid and its derivatives. The present invention satisfies this need and provides related advantages as well.

SUMMARY OF THE INVENTION

The invention provides a method of producing acrylic acid. The method includes contacting fumaric acid with a sufficient amount of ethylene in the presence of a cross-metathesis transformation catalyst to produce about two moles of acrylic acid per mole of fumaric acid. Also provided is an acrylate ester. The method includes contacting fumarate diester with a sufficient amount of ethylene in the presence of a cross-metathesis transformation catalyst to produce about two moles of acrylate ester per mole of fumarate diester. An integrated process for process for producing acrylic acid or acrylate ester is provided which couples bioproduction of fumaric acid with metathesis transformation. An acrylic acid and an acrylate ester production also is provided.

DETAILED DESCRIPTION OF THE INVENTION

Figure 1:
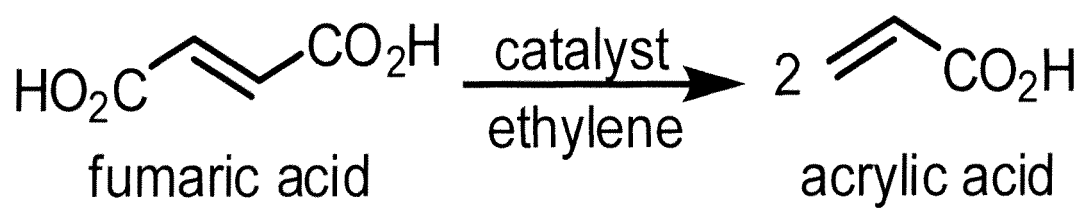
FIG. 1 is a schematic diagram showing the synthesis of acrylic acid through cross-metathesis between fumaric acid and ethylene (Scheme 1)

This invention is directed to a method of synthesis for acrylic acid and its derivatives. The method provides an efficient process for production of two moles of acrylic acid product per mole of fumaric acid reactant. The chemical synthesis method of the invention can be coupled with bioproduction of fumaric acid or fumarate ester for efficient utilization of carbon where one mole of a carbon source such as glucose can yield up to four moles of acrylic acid. Another particularly useful outcome of coupling a chemical synthesis step with bioproduction of a reactant intermediate is that it avoids possible toxic effects on production organisms that could result from the complete biosynthesis of acrylic acid or acrylate esters.

In one specific embodiment, the invention is directed to the chemical synthesis of acrylic acid or acrylate ester from fumaric acid or fumarate diester. The method utilizes cross-metathesis transformation to exchange double bonds between fumaric acid and ethylene, resulting in two moles of acrylic acid per mole of fumaric acid. With respect to acrylate ester formation, a cross-metathesis transformation is used to convert one mole of fumarate diester to two moles of acrylate ester. The ester group can include a wide range of different chemical moieties.

In another specific embodiment, the invention is directed to a process that couples a fumaric acid producing microbial organism with the chemical synthesis of acrylic acid or acrylate ester. The fumaric acid producing microbial organism contains a set of metabolic modifications that necessarily couple fumaric acid production to growth. Fumaric acid in the culture medium or fermentation broth can be converted directly to acrylic acid by cross-metathesis with ethylene, or first isolated with subsequent transformation. Acrylate esters are produced following diesterification of the biosynthesized fumaric acid.

As used herein, the term "acrylic acid" is intended to mean the carboxylic acid having the chemical formula $C_3H_4O_2$, a molecular mass of 72.06 g/mol with a melting point of 12° C. and a boiling point of 139° C. Acrylic acid is a clear, colorless liquid that is soluble, for example, in water and fully miscible in, for example, alcohols, ethers and chloroform. Acrylic acid is the simplest unsaturated carboxylic acid with both a double bond and a carboxyl group. Acrylic acid also is known in the art as 2-propenoic acid, propenoic acid, acroleic acid, ethylenecarboxylic acid, propene acid and vinylformic acid. The term is intended to include the acrylate ion and salt forms of acrylic acid.

As used herein, the term "acrylate ester" is intended to mean the ester form of acrylic acid. An ester is represented by the general chemical formula $RCO_2R'$ where R and R' can be the same or different, and can be either aliphatic or aromatic and wherein the aliphatic or aromatic moiety can be substituted or unsubstituted. For an acrylate ester, R corresponds to the ethyenyl (CH2=CH) moiety of the ester.

As used herein, the term "fumaric acid" is intended to mean the dicarboxylic acid having the chemical formula $C_4H_4O_4$, a molecular mass of 116.07 g/mol with a melting point of 287° C. and a white solid appearance. Fumaric acid is soluble, for example, in water and alcohols and is generally known to be a precursor to L-malate in the Krebs cycle and in various fermentation processes. Fumaric acid also is known in the art as (E)-butenedioic acid, trans-1,2-ethylenedicarboxylic acid, 2-butenedioic acid, allomaleic acid, boletic acid and lichenic acid. The term is intended to include the fumarate ion and salt forms of fumaric acid.

As used herein, the term "fumarate ester" is intended to mean an ester form of fumaric acid where R in the general chemical formula $RCO_2R'$ corresponds to the fumaric acid moiety and R' can be the same or different, and can be either aliphatic or aromatic and wherein the aliphatic or aromatic moiety can be substituted or unsubstituted. Because fumaric acid is a dicarboxylic acid a fumarate ester can include a R' moiety at either or both carboxyl groups. A fumarate ester having both carboxyl groups condensed into an ester is referred to herein as a "fumarate diester" and can be represented by the general formula $R1O_2CRCO_2R2$, where R corresponds to the ethenylene (CH=CH) moiety and R, R1 and R2 can be can be the same or different and can be either aliphatic or aromatic.

As used herein, the term "ethylene" is intended to mean the chemical compound having the formula $C_2H_4$, a molecular mass of 28.05 g/mol with a melting point of $^-$169.1° C. and a boiling point of $^-$103.7° C. Ethylene is a colorless flammable gas that exhibits solubility in water. Ethylene also is known in the art as ethene.

As used herein, the term "metathesis transformation," "cross-metathesis transformation" or a grammatically equivalent form thereof, is intended to mean a bimolecular process formally involving the exchange of a bond or bonds between similar interacting chemical species so that the bonding affiliations in the products are substantially the same or substantially similar to those in the reactants. A metathesis transformation can be schematically represented by the general reaction: RCH=CHR+R'CH=CHR'→RCH=R'CH+ RCH=R'CH. When used in reference to chemical conversion of fumaric acid or a fumarate ester or diester to acrylic acid, acrylate ester or 2 acrylate esters, respectively, the term is intended to mean the exchange of double bonds between fumaric acid, fumarate ester or fumarate diester and an alkene group. Metathesis transformations are well known in the art and can be found described in, for example, Grubbs, R. H. Olefin Metathesis. *Tetrahedron* 60:7117-40 (2004), and R. H. Grubbs, Handbook of Metathesis, Wiley-VCH. New York, 2003.

As used herein, the term "diesterification" is intended to mean an esterification reaction of a dicarboxylic acid to form a diester. An esterification reaction refers to a condensation reaction in which two molecules or moieties unite to form a single molecule with the loss of a small molecule such as water, hydrogen chloride, methanol or acetic acid, for example. Accordingly, diesterification of a fumaric acid of the invention condenses fumaric acid and an alcohol, for example, to form fumarate diester with the elimination of water.

A specific example of an esterification reaction include Fisher esterification, which refers to the process of forming an ester by refluxing a carboxylic acid and an alcohol in the presence of an acid catalyst. Catalysts well known in the art for Fisher esterification include, for example, sulfuric acid, p-toluene sulfonic acid and Lewis acids such as scandium(III) triflate. General reaction times can vary from about 1-10 hours at temperatures of 60-110° C. Esterification reactions are well known to those skilled in the art. Esterification reactions well known in the art other than Fisher esterification also can be used in an esterification reaction of the invention, such as reaction between a carboxylic acid chloride and an alcohol in the presence of a base such as pyridine, a tertiary amine, or aqueous sodium hydroxide. The last procedure is referred to commonly as the Schotten-Baumann reaction. Esterification reactions including mechanisms, substrates, reagents and conditions can be found described in, for example, Morrison and Boyd, *Organic Chemistry*, Sixth Edition, Prentice Hall, New Jersey (1992); Carey, F. A. and Sundberg, R. J., *Advanced Organic Chemistry*, Parts A and B, Third Edition, Plenum Press, New York (1990), and March's Advanced Organic Chemistry, 5th edition, 2001.

The term "esterification reagent" as it is used herein is intended to mean a chemical that is suitable for use in an esterification reaction. Therefore, esterification reagents include reactants such as a carboxylic acid and/or an alcohol as well as a catalyst or other chemically reactive compound that can be included in the chemical reaction. An esterification reagent also includes a diesterification reagent when used with a dicarboxylic acid. For example, the chemistry at one carboxyl group of the dicarboxylic acid fumaric acid of the invention is substantially the same as the chemistry at its second carboxyl group. Similarly, an esterification reagent also includes reagents that can react and form esters with more than two carboxyl groups on the same substrate. An example of a reactive compound is dicyclohexycarbodiimide, which acts as a dehydrating agent and facilitates esterification processes through formation of dicyclohexylurea.

As used herein, the term "catalyst" is intended to mean a substance that increases the rate of a chemical reaction without a net change in the amount of that substance in the system. Therefore, when used in reference to a cross-metathesis transformation the term is intended to refer to a substance that increases the rate of the bimolecular exchange of bonds but is not consumed in the transformation. A specific example of a class of metathesis transformation catalysts is the ruthenium metathesis catalysts which are described in, for example, Grubbs, R. H. supra; Bai et al., *Org. Biomol. Chem.* 3:4139-42 (2005), and Gibson et al., *Chem. Comm.*, 1107-08 (1997). When used in reference to an esterification reaction, including a diesterification reaction, the term is intended to refer to a substance that increases the rate of the condensation reaction without being consumed. Specific examples of esterification catalysts for Fisher esterification are exemplified above. These catalysts as well as others well known in the art for a variety of different types of esterification reactions also are described in, for example, March, supra; Morrison and Boyd, supra, and Carey, F. A. and Sundberg, R. J., supra.

As used herein, the term "sufficient amount" or a grammatically equivalent form thereof, when used in reference to a chemical reagent in a reaction or in reference to a culture constituent is intended to mean a quantity of the referenced regent or constituent that can meet the demands of the chemical reaction or cultured microbial organism. For example, a sufficient amount of a catalyst refers to a quantity of catalyst that is adequate to increase the referenced chemical reaction rate. A sufficient amount of, for example, a carbon source in a culture medium refers to a quantity that is adequate to support growth of a cultured microbial organism.

As used herein, the term "non-naturally" when used in reference to a microbial organism or microorganism of the invention is intended to mean that the microbial organism has at least one genetic alteration not normally found in a naturally occurring strain of the referenced species, including wild-type strains of the referenced species. "Wild-type," or grammatical equivalents thereof, refers to the common genotype or phenotype, or genotypes or phenotypes, of an organism as it is found in nature or in a standard laboratory stock for a given organism. Genetic alterations include, for example, a gene deletion or some other functional disruption of the genetic material. Genetic alterations also include modifications introducing expressible nucleic acids encoding metabolic polypeptides, other nucleic acid additions, nucleic acid deletions and/or other functional disruption of the microbial genetic material. Such modification include, for example, coding regions and functional fragments thereof, for heterologous, homologous or both heterologous and homologous polypeptides for the referenced species. Exemplary metabolic polypeptides include enzymes within a metabolic pathway or uptake pathway for one or more carbon sources used by a referenced microbial organism such as enzymes within the glycolysis or the pentose phosphate pathways.

As used herein, the terms "microbial organism," "microbe," "microbial" or "microorganism" is intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

An isolated microbial organism refers to an organism that is substantially free of at least one component of the referenced microbial organism as it is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsists in non-naturally occurring environments. Specific examples of isolated microbial organisms include partially pure microbial organism, substantially pure microbial organisms and microbial organisms cultured in a medium that is non-naturally occurring.

As used herein, the term "growth-coupled" when used in reference to the biosynthesis of a chemical compound or biochemical is intended to mean that the biosynthesis of the referenced molecule is an obligatory product produced during the growth phase of a microbial organism.

As used herein, the term "metabolic modification" is intended to refer to a biochemical reaction or transport process that is altered from its naturally occurring state. Metabolic modifications can include, for example, elimination of a biochemical reaction activity by functional disruptions of one or more genes encoding an enzyme participating in the reaction. Sets of exemplary metabolic modifications for microbial organisms having growth coupled production of fumaric acid are illustrated in Table 1 (starting at page 50). Individual reactions specified by such metabolic modifications and their corresponding gene complements are exemplified in Table 2 (starting at page 56) for *E. coli* as a representative microbial organism. Reactants and products utilized in these reactions are exemplified in Table 3 (starting at page 57).

As used herein, the term "gene disruption" or grammatical equivalents thereof, is intended to mean a genetic alteration that renders the encoded gene product inactive. The genetic alteration can be, for example, deletion of the entire gene, deletion of a regulatory sequence required for transcription or translation, deletion of a portion of the gene with results in a truncated gene product or by any of various mutation strategies that inactivate the encoded gene product. One particularly useful method of gene disruption is complete gene deletion because it reduces or eliminates the occurrence of genetic reversions in the non-naturally occurring microbial organisms of the invention.

As used herein, the term "stable" when used in reference to growth-coupled production of a biochemical product is intended to refer to microbial organism that can be cultured for greater than five generations without loss of the coupling between growth and biochemical synthesis. Generally, stable growth-coupled biochemical production will be greater than 10 generations, particularly stable growth-coupled biochemical production will be greater than about 25 generations, and more particularly, stable growth-coupled biochemical production will be greater than 50 generations, including indefinitely. Stable growth-coupled production of a biochemical can be achieved, for example, by deletion of a gene encoding an enzyme catalyzing each reaction within a set of metabolic modifications. The stability of growth-coupled production of a biochemical can be enhanced through multiple deletions, significantly reducing the likelihood of multiple compensatory reversions occurring for each disrupted activity.

Those skilled in the art will understand that the metabolic modifications exemplified herein are described with reference to *E. coli* genes and their corresponding metabolic reactions. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous gene disruptions in the other species. Such disruptions can include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the growth-coupled production of a biochemical product, those skilled in the art will understand that the orthologous gene harboring the metabolic activity to be disrupted is to be chosen for construction of the non-naturally occurring microbial organism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene compared to a gene encoding the function sought to be substituted. Therefore, a nonorthologous gene includes, for example, a paralog or an unrelated gene.

Therefore, in identifying and constructing the non-naturally occurring microbial organisms of the invention having growth-coupled production of a biochemical, those skilled in the art will understand with applying the teaching and guidance provided herein to a particular species that the identification of metabolic modifications should include identification and disruption of orthologs. To the extent that paralogs and/or nonorthologous gene displacements are present in the referenced microbial organism that encode an enzyme catalyzing a similar or substantially similar metabolic reaction, those skilled in the art also can eliminate these evolutionarily related genes to ensure that any functional redundancy in enzymatic activities do not short circuit the designed metabolic modifications.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compared and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarly to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

As used herein, the term "feedstock" refers to a substance used as a raw material in an industrial process. When used in reference to a culture of microbial organisms such as a fermentation process with cells, the term refers to the raw material used to supply a carbon or other energy source for the cells. A "renewable" feedstock refers to a renewable energy source such as material derived from living organisms or their metabolic byproducts including material derived from biomass, often consisting of underutilized components like chaff or stover. Agricultural products specifically grown for use as renewable feedstocks include, for example, corn, soybeans, switchgrass and trees such as poplar, primarily in the United States; wheat, flaxseed and rapeseed, primarily in Europe; sugar cane in Brazil and palm oil in South-East Asia. Therefore, the term includes the array of carbohydrates, fats and proteins derived from agricultural or animal products across the planet.

As used herein, the term "biomass" is intended to mean any plant-derived organic matter. Biomass available for energy on a sustainable basis includes herbaceous and woody energy crops, agricultural food and feed crops, agricultural crop wastes and residues, wood wastes and residues, aquatic plants, and other waste materials including some municipal wastes. Biomass feedstock compositions, uses, analytical procedures and theoretical yields are readily available from the U.S. Department of Energy and can be found described, for example, at the URL 1.eere.energy.gov/biomass/information_resources.html, which includes a database describing more than 150 exemplary kinds of biomass sources. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, sucrose, xylose, arabinose, galactose, mannose, fructose and starch. The term "biomass" also can be used to refer to a microbial population, e.g., the total microbial population of a fermeter during and after a fermentation process.

The invention provides a method of producing acrylic acid. The method includes contacting fumaric acid with a sufficient amount of ethylene in the presence of a cross-metathesis transformation catalyst to produce about two moles of acrylic acid per mole of fumaric acid.

Olefin metathesis and cross-metathesis has been one endeavor of chemical synthesis research for carbon-carbon bond and intermolecular carbon-carbon double bond formation of olefins (Grubbs, supra; Bai et al. supra, and Gibson et al., supra). However, these efforts have resulted with varying success. The chemical structures, substituents, stereochemistry and pKa's of the reactants have led to differing results (see, for example, see Chatterjee et al. *J. Am. Chem. Soc.* 125: 11360-70 (2003)). Predictability has only been obtained after exhaustive pathways of experimentation even for closely related molecules.

Fumaric acid and acrylic acid are classified as olefins due to their unsaturated hydrocarbon structure having the general formula $C_nFH_{2n}$. The chemical synthesis of acrylic acid or ester forms thereof have not been achieved through olefin cross-metathesis. In contrast however, it has been reported that dimethyl maleate, a cis isomer of dimethyl fumarate, displays low reactivity in olefin metathesis with ethylene. (Fomine, S, and Tlenkopatchev, M. A., *Org. Chem.* 691:5189-96 (2006)). Moreover, dimethyl fumarate has been reported to be unreactive toward terminal alkenes in cross-metathesis. (Chatterjee et al., supra). Without being bound by theory, it is generally understood that olefin metathesis is a substantially reversible process and therefore the products of a particular cross-metathesis often reflect statistical distributions governed by the relative thermodynamic energies of the various products and starting materials. In this respect, one skilled in the art will recognize an additional challenge in converting fumaric acid (or its diester) to acrylic acid (or its ester). Indeed the dimerization of acrylates to fumarates is well documented.

The reactant for the acrylic acid synthesis of the invention is fumaric acid, a dicarboxylic acid having pKa's of approximately 3.0 and 4.5. Cross-metathesis of diacids is not known to have been reported. Hence, the cross-metathesis transformation of the invention of fumaric acid to acrylic acid is unanticipated based on the historic course of research results in olefin cross-metathesis. The use of ethylene rather than terminal alkenes can positively affect the cross-metathesis of alkene substrates since the chain-carrying catalyst, [Ru=CH2], will contain the least sterically encumbered methylidene ligand attached to the ruthenium catalyst, thus providing for highly active catalysis (see, for example, Lloyd-Jones et al., *Chemie, Int.* Ed., 44, 7442-7 (2005)).

The acrylic acid synthesis method of the invention utilizes cross-metathesis between fumaric acid and ethylene. Fumaric acid is a dicarboxylic acid having a double bond between carbons C-2 and C-3. Cross-metathesis with ethylene splits this dicarboxylic acid into two molecules with the net formation of a double bond in each new molecule of acrylic acid. The net result is formation of two moles of acrylic acid per mole of fumaric acid reactant as shown in FIG. 1. Although fumaric acid cross-metathesis can be performed with a variety of olefins other than ethylene, the inclusion of ethylene creates a carbon-carbon double bond with formation of two moles of acrylic acid per mole of fumaric acid. Since both reactants are symmetric, only a single product (acrylic acid) is formed.

An exemplary reaction illustrating the cross-metathesis transformation of fumaric acid to two moles of acrylic acid is shown below. Briefly, acrylic acid having the following formula

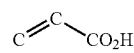

I can be manufactured by reacting fumaric acid having the following formula

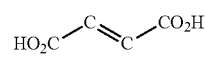

II with ethylene in the presence of an olefin metathesis catalyst to give the acrylic acid of formula I.

Cross-metathesis between fumaric acid and ethylene can be performed using a variety of synthesis methods and catalysts known in the art. Exemplary procedures and catalysts include, for example, any of those described in, for example, Grubbs, supra; Bai et al., supra; Gibson et al., supra, and Dias et al., *J. Am. Chem. Soc.,* 119:3887-3897 (1997). Such procedures can include reaction temperatures ranging from, for example, 0-100° C., pH ranges from about 2-10 and a variety of solvents including, for example, dichloromethane, dichloroethane, alcohols, water, other aqueous solutions, alcohol/water mixtures and the like.

Particularly useful catalysts include a variety of different species within the ruthenium class metathesis catalysts. Exemplary ruthenium based catalysts include, for example, phosphine-free ruthenium carbine complexes such as molybdenum alkoxyimidoalkylidene, ruthenium benzylidenes and ether-tethered ruthenium alkylidene derivatives; stable 16e ruthenium carbene complexes having the active bis(triphenylphosphine)-dichlororuthenium alkylidene complex, diazo compounds, ruthenium benzylidene complexes, ruthenium trichlorides prepared from late metal salts. A specific example of a phosphine-free carbene ruthenium catalysts is [1,3-bis(2,6-dimethylphenyl)4,5-dihydroimidazol-2-ylidene]$C_5H_5N)_2(Cl)_2Ru$=CHPh, which is a bispyridine complex. A further specific example of a ruthenium based catalyst is $Cl_2(PCy_3)_2Ru$=CHPh.

Other examples of cross-metathesis catalysts applicable for use in the synthesis methods of the invention include, for example, high oxidation state late metal complexes such as those described by Tebbe et al. *J. Am. Chem. Soc.*, 101:5075 (1979) Wengrovius et al., *J. Am. Chem. Soc.*, 102:4515 (1980), and Osborn et al., *Chem. Commun.*, 431-432 (1980); titanium methylene complex or Tebbe Reagent (Pine et al., *J. Am. Chem. Soc.*, 102:3270 (1980); unsymmetrical Tebbe complexes (Howard et al., *J. Am. Chem. Soc.*, 102:6876 (1980); metallacyclobutane (Kress et al., *J. Am. Chem. Soc.*, 109:899 (1987); Wengrovius et al., *J. Am. Chem. Soc.*, 102: 4515-4516 (1980), and Quignard et al., *Angew. Chem. Int. Ed. Engl.*, 31(5):628-631 (1992)); and/or tungsten and molybdenum alkylidene complexes that contained bulky imido ligands (Schrock et al., *J. Am. Chem. Soc.*, 110:1423-1435 (1988)).

Additional catalysts useful in the olefin cross-metathesis reaction of the invention can be exemplified, but not limited to, the following:

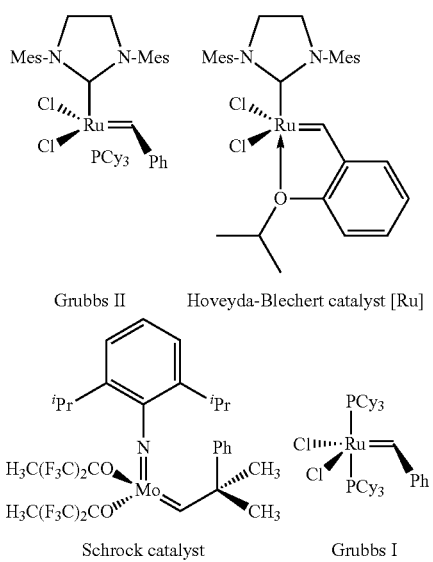

Grubbs II  Hoveyda-Blechert catalyst [Ru]

Schrock catalyst  Grubbs I

Selection of optimal catalysts to use in the cross-metathesis reactions of the invention can readily be performed by those skilled in the art. For example, catalysts having admirable activity in a particular solution, pH and/or temperature can be selected by contacting a fumaric acid, fumarate monoester or fumarate diester substrate in the presence of ethylene and measuring the rate of acrylic acid or acrylate ester product formation. Any of the catalysts exemplified above can be screened for optimal activity as well as others known in the art. Selection of one or more optimal catalysts can be beneficial for identifying cross-metathesis catalysts exhibiting enhanced catalytic rates.

Figure 2:
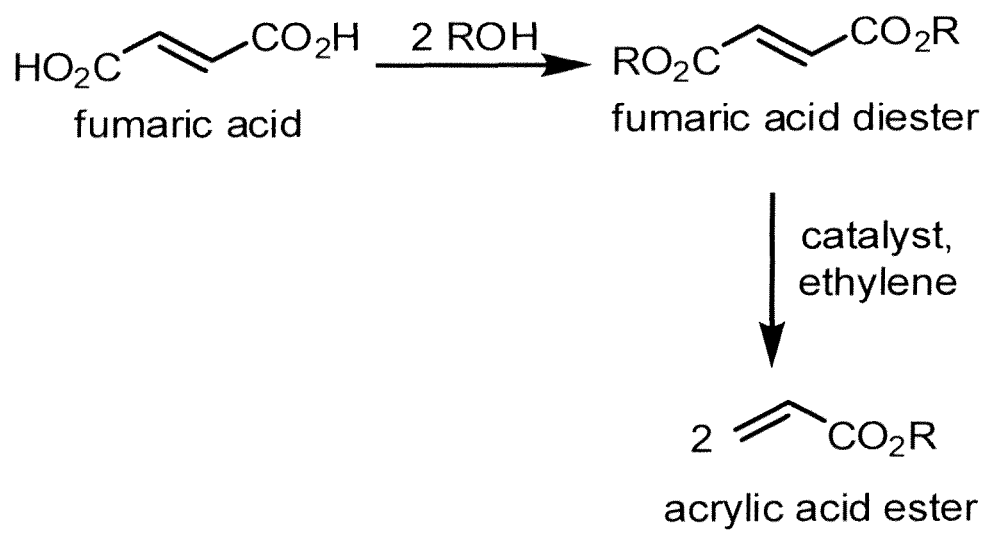
FIG. 2 is a schematic diagram showing the synthesis of acrylate ester through cross-metathesis between fumarate diester and ethylene (Scheme 2)

The cross-metathesis synthesis method of the invention also can be employed with fumarate ester or a fumarate diester and ethylene to produce acrylate esters. In the former reaction, cross-metathesis with a fumarate monoester will produce one mole of acrylic acid and one mole of acrylate ester per mole of fumarate monoester. In the later reaction, the net result is formation of two moles of acrylate ester per mole of fumarate diester reactant as shown in FIG. 2.

An exemplary reaction illustrating the cross-metathesis transformation of fumarate ester to two moles of acrylate ester is shown below. Briefly, acrylate ester having the following formula

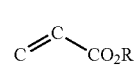

III wherein R represents straight or branched alkyl having 1 to 10 carbon atoms wherein said alkyl may be optionally and independently substituted with alkyl having 1 to 10 carbon atoms: phenyl; phenylalkyl; amino; hydroxy; alkylamino having 1 to 10 carbon atoms; and alkoxy having 1 to 10 carbon atoms or R represents cycloalkyl having 3 to 6 ring carbon atoms wherein said ring carbon atoms may be optionally and independently substituted with alkyl having 1 to 6 carbon atoms and hydroxy can be manufactured by reacting a fumarate diester having the following formula

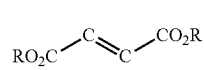

IV wherein R is defined as above with ethylene in the presence of a olefinic metathesis catalyst to give the acrylate ester of formula III.

Given the teachings and guidance provided herein, those skilled in the art will understand that the fumaric acid, fumarate diester, acrylic acid and acrylate ester of the present invention can be further substituted by aliphatic and/or aromatic moieties. For example, C-2 and C-3 carbons of fumarate diester can be substituted with methyl. In this specific embodiment, cross-metathesis with ethylene will produce methacrylate ester. In like fashion, the C-2 and/or C-3 also can be substituted with, for example, other alkyl such as ethyl, propyl or butyl and subjected to cross-metathesis to yield the corresponding alkyl substituted acrylate ester. Those skilled in the art will understand that corresponding metathesis transformations also can be performed with fumaric acid similarly substituted. Those skilled in the art also will understand that the above described aliphatic and/or aromatic substituted moieties themselves can additionally be further substituted.

In addition to the further substitution of fumaric acid, fumarate diester, acrylic acid and acrylate ester of the present invention described above, those skilled in the art also will understand that the ethylene metathesis reactant also can be further substituted. In this regard, a wide variety of disubstituted alkeynes can be employed in the cross-metathesis reactions of the invention to yield chemical compounds other than acrylic acid or acrylate ester. Such disubstituted alkeynes can be represented by the chemical formula RCH=CHR', where R and R' can be the same or different chemical moiety, including hydrogen and any straight or branched alkyl. A specific example of such a disubstituted alkeyne is 2-butene. By exemplification to cross-metathesis with fumaric acid, where R is hydrogen the product is acrylic acid. In comparison, where R is methyl, the product is crotanoic acid.

Fumarate mono- and diesters can be produced by a variety of esterification methods well known in the art. A useful esterification method is treatment of fumaric acid with an alcohol in the presence of a mineral acid such as sulfuric acid or dry hydrogen chloride. While the choice of alcohol will be determined by the type of ester or diester desired, it is to be understood that primary, secondary or tertiary aliphatic or aromatic, substituted or unsubstituted alcohols are contemplated by this invention. Those skilled in the art will know, or can readily determine, what alcohol or alcohols can be selected for use with a particular type of ester or diester.

A particularly useful esterification method is treatment of fumaric acid having the following formula

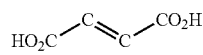

with an alcohol having the formula ROH, wherein R is represented by straight or branched alkyl having 1 to 10 carbon atoms wherein said alkyl may be optionally and independently substituted with alkyl having 1 to 10 carbon atoms; phenyl; phenylalkyl; amino; hydroxy; alkylamino having 1 to 10 carbon atoms; and alkoxy having 1 to 10 carbon atoms or R represents cycloalkyl having 3 to 6 ring carbon atoms wherein said ring carbon atoms may be optionally and independently substituted with alkyl having 1 to 6 carbon atoms and hydroxy in the presence of a mineral acid.

While the above esterification method describes treatment of fumaric acid with an alcohol in the presence of a mineral acid to arrive at the fumaric diester, it is also understood that the fumaric acid can be converted into an acid chloride which can then be treated with an alcohol to arrive at the ester or diester. One benefit of the two-step reaction as opposed to the direct esterification method is that the reversibility of the direct ester route is avoided.

The invention also provides a process for producing acrylic acid. The process includes: (a) culturing in a sufficient amount of nutrients and media a non-naturally occurring microbial organism having a set of metabolic modifications obligatorily coupling fumaric acid production to growth of the microbial organism, the set of metabolic modifications includes disruption of at least one of the gene sets having: (1) fumABC, zwf, purU, or (2) fumABC, zwf, glyA, or an ortholog thereof, to produce stable growth-coupled production of fumaric acid, and (b) contacting the fumaric acid with a sufficient amount of ethylene in the presence of a cross-metathesis transformation catalyst to produce about two moles of acrylic acid per mole of fumaric acid.

Figure 3:
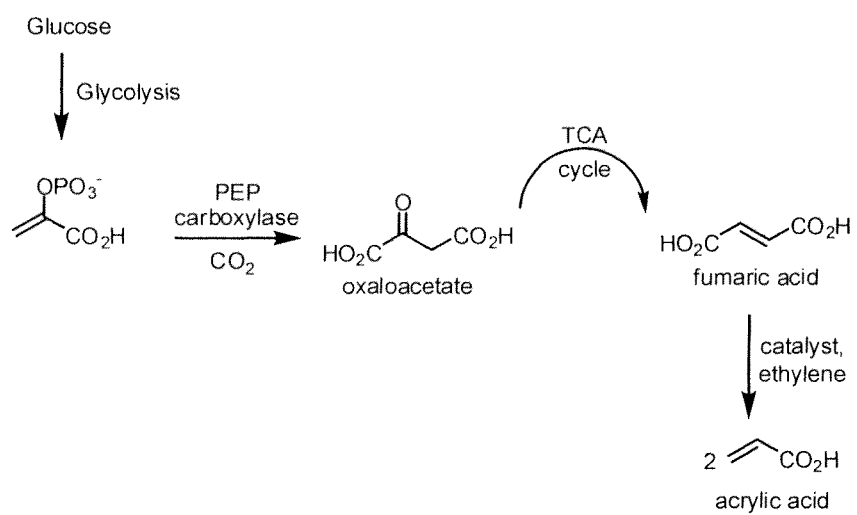
FIG. 3 is a schematic diagram showing an integrated bioproduction system for acrylic acid from glucose through biosynthesis of fumaric acid.

A further embodiment of the invention includes coupling fumaric acid substrate biosynthesis with chemical synthesis of acrylic acid or acrylate esters in an integrated process. FIG. 3 illustrates one approach for integrated production of acrylic acid from the biosynthesis of fumaric acid substrate. Those skilled in the art will understand that although the integration of substrate production through a bioprocess such as fermentation and final product manufacture through one or more chemical synthesis procedures is illustrated herein with respect to biosynthesis of fumaric acid, given the teachings and guidance provided herein, any combination or permutation of biosynthesis to one or more intermediates and chemical synthesis of final product can be accomplished using the process of the invention. Given the teachings and guidance provided herein, those skilled in the art also will understand that a chemical synthesis step can be utilized in synthesis of one or more intermediates to a final product. Similarly, those skilled in the art also can employ a genetic modifications and biosynthesis to accomplish the conversion of fumaric acid to acrylic acid. Accordingly, the integrated process shown in FIG. 3 illustrating biosynthesis from a glucose carbon source to the acrylic acid using fumaric acid as an intermediate substrate is exemplary. Therefore, genetic modifications resulting in entry and flux through any portion of glycolysis, TCA or other metabolic pathways that result in increased fumaric acid production can be employed in a process of the invention for production of acrylic acid and acrylate esters of the invention.

Useful embodiments of an integrated process of the invention is the bioproduction of a genetically engineered product which is a substrate or intermediate to olefin metathesis. In this regard, fermentation of non-naturally occurring organisms modified to biosynthesize specific products are particularly useful sources for chemical compounds such as fumaric acid and other olefins. Given the teachings and guidance provided herein, those skilled in the art will understand that the integrated process exemplified herein with respect to the olefin fumaric acid and the cross-metathesis transformation to acrylic acid can be equally applied to produce essentially any olefin of interest. Such olefins can be coupled to a metathesis transformation for the chemical synthesis of a wide variety of other olefins. Those skilled in the art also will understand that the integrated process coupling bioproduction by, for example, fermentation of an olefin substrate to a metathesis transformation also can be employed in the production of an olefin intermediate. The intermediate can be chemically converted to an olefin that can serve as a substrate for olefin metathesis.

Specific examples of coupling an olefin product of bioproduction such fermentation to olefin metathesis is the production of the olefin fumaric acid and cross-metathesis to acrylic acid and other compounds as described previously. Specific examples of coupling a product of bioproduction such as fermentation to yield an intermediate to olefin metathesis are exemplified below. Chemical conversion of such intermediates to an olefin yields substrates useful in olefin metathesis and also can be performed in an integrated process as described previously and below. For example, 3-hydroxypropionic acid (3-HP) can be produced by fermentation of 3-HP producing microbial organisms and dehydrated to the olefin acrylic acid. The acrylic acid can be subjected to metathesis with an olefin of interest to produce a desired olifen product. Similarly, 2,3-butane diol also can be produced by fermentation using the teachings and guidance provided herein. The 2,3-butane diol intermediate can be further dehydrated into butadiene which can be employed as an olefin substrate to make a wide range of olefin products through metathesis transformation.

Therefore, the invention provides a process for producing an olefin. The process includes: (a) culturing by fermentation in a sufficient amount of nutrients and media a microbal organism that produces a first olefin, and (b) contacting the first olefin with a sufficient amount of a disubstituted alkeyne in the presence of an olefin metathesis transformation catalyst to produce second, different olefin. The disubstituted alkeyne can be ethylene. The microbial organism of can be, for example, a non-naturally occurring microbal organism such as an organism genetically engineered to produce the first olefin, or a naturally occurring microbial organism such as an organism that naturally produces the first olefin.

The invention further provides a process for producing an olefin. The process includes: (a) culturing by fermentation in a sufficient amount of nutrients and media a microbal organism that produces an olefin intermediate; (b) performing a chemical modification to convert the olefin intermediate to a first olefin, and (c) contacting the first olefin with a sufficient amount of a disubstituted alkeyne in the presence of an olefin metathesis transformation catalyst to produce second, different olefin. The chemical modification can be, for example, dehydrogenation. The disubstituted alkeyne can be ethylene. The microbial organism of can be, for example, anon-naturally occurring microbial organism such as an organism genetically engineered to produce the olefin intermediate, or a naturally occurring microbial organism such as an organism that naturally produces the olefin intermediate.

Step 1 illustrated in FIG. 3 exemplifies biological production of fumaric acid, which derives from the TCA cycle and is a common intermediate of central cellular metabolism. Central metabolites are particularly useful targets for metabolic engineering as they are often constitutively produced during basal metabolism.

Step 2 of the integrated process illustrated in FIG. 3 exemplifies the coupling of olefin cross-metathesis involving ethylene as described previously and shown in FIG. 1. In one embodiment, coupling of the bioproduction of fumaric acid and cross-metathesis is performed by direct addition of a selected cross-metathesis catalyst and ethylene to the fumaric acid culture or fermentation broth. Such direct coupling is an efficient and streamlined manufacturing process of acrylic acid. Olefin metathesis based upon ruthenium catalysts has been shown to perform well in water (see, for example, Lynn et al., *J. Am. Chem. Soc.*, 118:784-90 (1996) and Lynn et al. *J. Am. Chem. Soc.* 120:1627-28 (1998). In another embodiment, fumaric acid can be isolated from the culture medium or fermentation broth and reacted separately with a cross-metathesis catalyst and ethylene to synthesize acrylic acid.

Integrating biosynthesis of fumaric acid and chemical cross-metathesis transformation with ethylene, for example, to produce acrylic acid is additionally useful because it results in a highly efficient conversion of substrate carbon (e.g., glucose or sucrose) into the desired product (e.g., acrylic acid). Similarly, coupling of esteritication, including diesterification, of fumaric acid to fumarate mono or diester also yields the same carbon utilization efficiencies. For example, carbon from 1 mole of glucose entering the glycolysis metabolic pathway provides two moles of phosphoenol pyruvate (PEP), which reacts with carbon dioxide via PEP carboxylase to result in a maximum theoretical yield of approximately 2.0 moles of fumaric acid. Upon cross-metathesis with ethylene, each mole of fumaric acid yields two moles of acrylic acid, resulting a process where one mole of glucose and 2.0 moles of ethylene are converted into up to four moles of acrylic acid.

Another particularly useful attribute of the integrated process of the invention illustrated in FIG. 3 is that any thermodynamic constraints encountered in the production of acrylic acid directly from glucose by fermentation as well as possible toxicity of acrylic acid to the host organism can be avoided. The integrated process of the invention biologically produces fumaric acid, which is a normal metabolic intermediate, and then transforms fumaric acid to acrylic acid in a post-culture or post-fermentation step, thus avoiding exposure of the production organisms to, for example, a lethal fermentation product.

In one embodiment, the fumaric acid producing microbial organisms that can be used in an integrated process of the invention include isolated organisms that naturally produce fumaric acid. In another embodiment, the fumaric acid producing microbial cells can be genetically engineered for enhanced expression of fumaric acid. Particularly useful engineered microbial organisms include metabolic modifications that couple organism growth to product biosynthesis.

For the integrated production process of acrylic acid and/or acrylate ester of the invention, the biosynthetic product is fumaric acid.

Growth coupled production of fumaric acid can be accomplished by, for example, identifying metabolic modifications that obligatory couple fumaric acid to growth. Particularly useful methods that can be employed to accurately predict biological behavior in response to genetic changes include in silico methods such as those exemplified further below and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. Such method include in silky) construction, optimization and modifications of metabolic and regulatory networks including, for example, identification of gene sets that when disrupted obligatory couple growth to fumaric acid production. Once identified, the set of reactions that are to be disrupted in order to achieve growth-coupled fumaric acid production are implemented in the target cell or organism by functional disruption of at least one gene encoding each metabolic reaction within the set.

As described previously, one particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the fumaric acid coupling are desired or when genetic reversion is less likely to occur. Those skilled in the art also will understand that any molecular design and recombinant implementation, for example, can be used to add, delete or substitute one or more genes encoding enzymes in a metabolic pathway to confer a desired activity onto the host organism. Therefore, although the non-naturally occurring microbial organisms of the invention are exemplified herein with respect to disruption of genes to generate a metabolic network obligatory coupling fumaric acid to growth, those skilled in the art will understand that the non-naturally occurring microbial organisms of the invention also include genetic modifications that confer a desired metabolic activity by, for example, introduction of one or more metabolic activities into a host microbial organism.

Briefly, with respect to introducing one or more desired metabolic activities, those skilled in the art will understand that the number of encoding nucleic acids to introduce in an expressible form will parallel the deficiencies in the target pathway to be constructed. Therefore, one or more host microbial organisms for use in the integrated process of the invention can have one, two, three, four, five or six encoding nucleic acids encoding the enzymes constituting the target product biosynthetic pathway or pathways. In some embodiments, the host microbial organism or organisms also can include other genetic modifications that facilitate or optimize target product biosynthesis or that confer other useful functions onto the host microbial organism.

Sources of encoding nucleic acids which can be used for generating the various metabolic modifications including, for example, expression of heterologous metabolic polypeptides, effecting targeted disruptions of metabolic genes or for other recombinantly engineered modifications exemplified herein can include, for example, any species where the encoded gene product is capable of catalyzing the referenced reaction or activity. Such species include both prokaryotic and eukaryotic organisms including, but not limited to, bacteria, archaea, eubacteria, animal, mammal, including human.

Methods for constructing and testing the expression levels of any of the non-naturally occurring microbial organisms, including those modified to synthesize an encoding polypeptide as well as conformation that disrupted genes reduce or eliminate expression of the encoded polypeptide, can be performed, for example, by recombinant procedures and detection methods well known in the art. Such methods can be found described in, for example, Sambrook et al., *Molecular Cloning: A Laboratory Manual*, Third Ed., Cold Spring Harbor Laboratory, New York (2001); Ausubel et al., *Current Protocols in Molecular Biology*, John Wiley and Sons, Baltimore, Md. (1999).

Employing the methods exemplified above and further below, metabolic modifications have been identified that obligatory couple the production of fumaric acid to microbial organism growth. Microbial organism strains constructed with the identified metabolic modifications produce elevated levels of fumaric acid during the exponential growth phase. These strains can be beneficially used for the commercial production of fumaric acid in, for example, continuous fermentation process without being subjected to the negative selective pressures described previously. Such production can be coupled with cross-metathesis transformation or with diesterification followed by cross-metathesis transformation in an integrated process for efficient production of acrylic acid and acrylate esters, respectfully.

Non-naturally occurring microbial organisms of the invention include bacteria, yeast, fungus or any of a variety of other microbial organisms applicable to fermentation processes. Exemplary bacteria include species selected from *E. coli, A. succiniciproducens, A. succinogenes, M. succiniciproducens, R. etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens,* and *Pseudomonas putida*. Exemplary yeasts include species selected from *Saccharomyces cerevisiae, Schizosaccharomyces pombe, Kluyveromyces lactis, Kluyveromyces marxianus, Aspergillus terreus, Aspergillus niger, Rhizopus arrhizus, Rhizopus oryzae,* and *Pichia pastoris*. With respect to the integrated process of the invention described further below, microbial organisms that tolerate low pH are particularly useful due to the avoidance of any desired neutralization steps and the lowering of salt formation associated with acid production using acid-intolerant organisms. Microbial organisms tolerant to pH of about 3.0 or less can be used if these characteristics are desirable in an integrated process of producing acrylic acid and/or acrylate esters. However, microbial organisms that tolerate pH values of about 6.0, 5.5, 5.0. 4.5, 4.0 or 3.5 or less, including all pH values in between or below these exemplary values, also can be used as well.

The microbial organisms having growth-coupled fumaric acid production are exemplified herein with reference to an *E. coli* genetic background. However, with the complete genome sequence available for now more than 550 species (with more than half of these available on public databases such as the NCBI), including 395 microbial organism genomes and a variety of yeast, fungi, plant, and mammalian genomes, the identification of an alternate species homolog for one or more genes, including for example, orthologs, paralogs and nonorthologous gene displacements, and the interchange of genetic alterations between organisms is routine and well known in the art. Accordingly, the metabolic modifications enabling growth-coupled production of fumaric acid described herein with reference to a particular organism such as *E. coli* can be readily applied to other microbial organisms, including prokaryotic and eukaryotic organisms alike. Given the teachings and guidance provided herein, those skilled in the art will know that a metabolic modification exemplified in one organism can be applied equally to other organisms.

For example, fumaric acid production can be coupled to exponential growth in *E. coli* by deletion or functional removal of one or more genes encoding enzymes catalyzing the reaction referred to herein as FUM, one or more genes encoding enzymes catalyzing the reaction referred to herein as PGDH, and one or more genes encoding enzymes catalyzing the reaction referred to herein as FTHFD. As shown in Table 2, *E. coli* genes that encode an enzyme catalyzing the FUM reaction is fumABC or b1611, b1612 and b4122. Also, shown in Table 2 is an *E. coli* gene that encodes an enzyme catalyzing the PGDH reaction. This PDGH associated gene is gnd or b2029. Similarly, the *E. coli* gene encoding the enzyme catalyzing the FTHFD reaction is purU or b1232. To produce a metabolically engineered *E. coli* exhibiting growth coupled succinate production, genes encoding at least one enzyme catalyzing each of the FUM, PGDH and FTHFD reactions have to be functionally disrupted. The disruption of these genes should include orthologs. Such a disruption can occur, for example, by deleting any of the fumAB or C genes (b1611, b1612 and b4122) and the gnd (b2029) and the purU (b1232) genes. For the growth-coupled production of fumaric acid in a cell or organism other then *E. coli* the genes encoding comparable reactions for FUM, PGDH and FTHFD in the species of interest can be functionally disrupted. For those organisms having analogous metabolic pathways such disruption can be accomplished by deleting, for example, the species homologue to the fumAB or C genes (b1611, b1612 and b4122) and the gnd (b2029) and the purU (b1232) genes.

As described previously, such homologues can include othologs and/or nonorthologous gene displacements. In some instances, such as when a substitute metabolic pathway exists in the species of interest, functional disruption can be accomplished by, for example, deletion of a paralog that catalyzes a similar, yet non-identical metabolic reaction which replaces the referenced reaction. Because certain differences among metabolic networks between different organisms, those skilled in the art will understand that the actual genes disrupted between different organisms may differ. However, the given the teachings and guidance provided herein, those skilled in the art also will understand that the methods of the invention can be applied to all microbial organisms to identify the cognate metabolic modifications between organisms and to construct an organism in a species of interest that will enhance the coupling of fumaric acid biosynthesis to growth.

The fumaric acid producing organisms of the invention will be described herein with general reference to the metabolic reaction, reactant or product thereof, or with specific reference to one or more genes associated with the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction and that reference to any of these metabolic constitutes also references the gene or genes encoding the enzymes that catalyze the referenced reaction, reactant or product. Likewise, given the well known fields of metabolic biochemistry, enzymology and genomics, reference herein to a gene also constitutes a reference to the corresponding encoded enzyme and the reaction it catalyzes as well as the reactants and products of the reaction. Exemplary reactions, reaction nomenclature, reactants, products, cofactors and genes encoding enzymes catalyzing a reaction involved in the growth-coupled production of fumaric acid are set forth in Tables 1, 2 and 3.

Sets of metabolic modifications or transformations that result in elevated levels of fumaric acid biosynthesis during exponential growth are exemplified in Table 1. Each modification within a set corresponds to the requisite metabolic reaction that should be functionally disrupted. Functional disruption of all reactions within each set results in the obligatory production of fumaric acid by the engineered strain during the growth phase. The corresponding reactions to the referenced modifications in Table 1, and the gene or genes that potentially encode them in *E. coli*, are set forth in Table 2. Table 3 provides the full biochemical names for the reactants, cofactors and products referenced in the reactions of Table 2.

For example, for each strain exemplified in Table 1, the metabolic modifications that can be generated for growth coupled fumaric acid production are shown in each row. These modifications include the functional disruption of from one to six or more reactions. In particular, 187 strains are exemplified in Table 1 that have non-naturally occurring metabolic genotypes. Each of these non-naturally occurring modifications result in an enhanced level of fumaric acid production during the exponential growth phase of the microbial organism compared to a wild-type strain, under appropriate culture conditions. Appropriate conditions include, for example, those exemplified further below in the Examples such as particular carbon sources or reactant availabilities and/or adaptive evolution.

Given the teachings and guidance provided herein, those skilled in the art will understand that to disrupt an enzymatic reaction it is necessary to disrupt the catalytic activity of the one or more enzymes involved in the reaction. Disruption can occur by a variety of means including, for example, deletion of an encoding gene or incorporation of a genetic alteration in one or more of the encoding gene sequences. The encoding genes targeted for disruption can be one, some, or all of the genes encoding enzymes involved in the catalytic activity. For example, where a single enzyme is involved in a targeted catalytic activity disruption can occur by a genetic alteration that reduces or destroys the catalytic activity of the encoded gene product. Similarly, where the single enzyme is multimeric, including heteromeric, disruption can occur by a genetic alteration that reduces or destroys the function of one or all subunits of the encoded gene products. Destruction of activity can be accomplished by loss of the binding activity of one or more subunits in order to form an active complex, by destruction of the catalytic subunit of the multimeric complex or by both. Other functions of multimeric protein association and activity also can be targeted in order to disrupt a metabolic reaction of the invention. Such other functions are well known to those skilled in the art. Further, some or all of the functions of a single polypeptide or multimeric complex can be disrupted according to the invention in order to reduce or abolish the catalytic activity of one or more enzymes involved in a reaction or metabolic modification of the invention. Similarly, some or all of enzymes involved in a reaction or metabolic modification of the invention can be disrupted so long as the targeted reaction is destroyed.

Given the teachings and guidance provided herein, those skilled in the art also will understand that an enzymatic reaction can be disrupted by reducing or eliminating reactions encoded by a common gene and/or by one or more orthologs of that gene exhibiting similar or substantially the same activity. Reduction of both the common gene and all orthologs can lead to complete abolishment of any catalytic activity of a targeted reaction. However, disruption of either the common gene or one or more orthologs can lead to a reduction in the catalytic activity of the targeted reaction sufficient to promote coupling of growth to fumaric acid biosynthesis. Exemplified herein are both the common genes encoding catalytic activities for a variety of metabolic modifications as well as their orthologs. Those skilled in the art will understand that disruption of some or all of the genes encoding a enzyme of a targeted metabolic reaction can be practiced in the methods of the invention and incorporated into the non-naturally occurring microbial organisms of the invention in order to achieve the growth-coupled fumaric acid production.

Therefore, the invention further provides a non-naturally occurring microbial organism having a set of metabolic modifications obligatory coupling fumaric acid production to growth of said microbial organism. The set of metabolic modifications include disruption of one or more genes encoding an enzyme catalyzing each reaction selected from the set of reactions including:

(a) FUM (fumABC), PGDH (gnd), FTHFD (purU); (Strain A)

(b) FUM (fumABC), PGDH (gnd), FTHFD ((purU), ACKr (ackA-pta); (Strain B)

(c) FUM (fumABC), PGDH (gnd), GHMT2 (glyA); (Strain C)

(d) FUM (fumABC), PGDH (gnd), GHMT2(glyA), GLCpts (ptsG); (Strain D)

(e) FUM (fumABC), PGDH (gnd), FTHFD (purU), GLUDy (gdhA); (Strain E)

(f) FUM (fumABC), PGDH (gnd), FTHFD (purU), THD2 (pntAB); (Strain F)

(g) FUM (fumABC), FTHFD (purU), THD2 (pnAB), ACKr (ackA-pta), PGM (yibO), PGL (ybhE); (Strain G)

wherein the microbial organism exhibits stable growth-coupled production of fumaric acid. The common names for the genes encoding the enzymes responsible for catalyzing the specified reactions are shown in parenthesis.

In the non-naturally occurring microbial organisms having the metabolic modification (a) FUM, PGDH, FTHFD, (b) FUM, PGDH, FTHFD, ACKr or (d) FUM, PGDH, GHMT2, GLCPts, fumA, fumB, and fumC are genes encoding separate enzymes potentially capable of carrying out the FUM reaction. Thus at least one and possibly all three, fumA, fumB, and fumC must be removed to prevent FUM from uncoupling fumaric acid production from cell growth. Alternatively, the reaction GLCpts is carried out by a protein complex encoded by multiple genes. Deleting one or a combination of genes from the pts gene cluster, is thus sufficient for disrupting the GLCpts reaction.

Briefly, with respect to the genes exemplified above and their relationship to their cognate subunits within multimeric complexes, their orthologs and the reactions catalyzed by their gene products, FUM by the enzyme encoded by b1611, b1612, and b4122, PGDH is encoded by the product of one gene, b2029 (gnd) and FTHFD activity by purU (b1232). ACKr is encoded by the product of one gene, b2296 (ackA-pta), which has an ortholog b3115. GHMT2 is encoded by the product of the gene: b2551 (glyA). GLCpts activity requires enzyme subunits encoded by nine genes: b2415, b2416, b2417, b1817, b1818, b1819, b1101, b0679, and b1621 (represented collectively as ptsG). THD2 is the reaction product of a complex encoded by the genes pntA (b1603) and pntB (b1602). Since the reactions THD2 and GLCpts are carried out by protein complexes encoded by multiple genes, deleting one or a combination of genes from the pts and pnt gene clusters is thus sufficient for disrupting the reactions. GLUDy is catalyzed by an enzyme encoded by the gene gdhA (b1761). The PGM and PGL activities are a function of the enzymes encoded by b3612 and b0767 respectively.

As described above, functional disruption of the above metabolic reactions to yield fumaric acid producing microbial organisms also can be accomplished by substituting the gnd gene with the zwf gene for elimination of the PGDH reaction. Employing this gene substitution yields the following metabolic modifications which disrupt the enzymes catalyzing the reactions set forth for Strains A-G, above:

(a) fumABC, zwf, purU (strain A)
(b) fumABC, zwf, purU, ackA-pta (B)
(c) fumABC, zwf, glyA (C)
(d) fumABC, zwf, glyA, ptsG (D)
(e) fumABC, zwf, purU, gdhA (E)
(f) fumABC, zwf, purU, pntAB (F)
(g) fumABC, pntAB, purU, ackA-pta, yibO, ybhE (G)

Two common sets of gene deletions within the above exemplified strains that can be used for example to generate fumaric acid producing microbial organism include:

(a) fumABC, zwf, purU
(b) fumABC, zwf, glyA.

Accordingly, a non-naturally occurring microbial organism having a set of metabolic modifications coupling fumaric acid production to growth of the microbial organism is provided where the set of metabolic modifications includes disruption of one or more genes selected from the gene sets including: (a) fumABC, zwf, purU and (b) fumABC, zwf, glyA, or an ortholog thereof, wherein the microbial organism exhibits stable growth-coupled production of fumaric acid. Additionally provided is a non-naturally occurring microbial organism having the genes encoding the metabolic modification (a) fumABC, zwf, purU that further includes disruption of at least one gene selected from (1) ackA-pta, (2) gdhA, (3) pntAB and (4) ackA-pta, yibO, ythE.

Given the teachings and guidance provided herein, those skilled in the art will understand that a wide variety of combinations and permutations exist for the non-naturally occurring microbial organisms useful in the methods and processes of the invention. One computational particularly useful method for identifying and designing metabolic modifications favoring biosynthesis of a product is the OptKnock computational framework, Burgard et al., *Biotechnol Bioeng*, 84: 647-57 (2003). OptKnock is a metabolic modeling and simulation program that suggests gene deletion strategies that result in genetically stable microbial organisms which overproduce the target product. Specifically, the framework examines the complete metabolic and/or biochemical network of a microbial organism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of fumaric acid or used in connection with the non-naturally occurring microbial organisms for further optimization of fumaric acid biosynthesis.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that enable an effective query of the performance limits of metabolic networks and provides methods for solving the resulting mixed-integer linear programming problems. The metabolic modeling and simulation methods referred to herein as OptKnock are described in, for example, U.S. patent application Ser. No. 10/043,440, filed Jan. 10, 2002, and in International Patent No. PCT/US02/00660, filed Jan. 10, 2002.

Another computational method for identifying and designing metabolic modifications favoring biosynthetic production of a product is metabolic modeling and simulation system termed SimPheny®. This computational method and system is described in, for example, U.S. patent application Ser. No. 10/173,547, filed Jun. 14, 2002, and in International Patent Application No. PCT/US03/18838, filed Jun. 13, 2003.

SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components. Analysis methods such as convex analysis, linear programming and the calculation of extreme pathways as described, for example, in Schilling et al., *J. Theor. Biol.* 203:229-248 (2000); Schilling et al., *Biotech. Bioeng.* 71:286-306 (2000) and Schilling et al., *Biotech. Prog.* 15:288-295 (1999), can be used to determine such phenotypic capabilities. As described in the Examples below, this computation methodology was used to identify and analyze the feasible as well as the optimal 4-HB biosynthetic pathways in 4-HB non-producing microbial organisms.

As described above, one constraints-based method used in the computational programs applicable to the invention is flux balance analysis. Flux balance analysis is based on flux balancing in a steady state condition and can be performed as described in, for example, Varma and Palsson, *Biotech. Bioeng.* 12:994-998 (1994). Flux balance approaches have been applied to reaction networks to simulate or predict systemic properties of, for example, adipocyte metabolism as described in Fell and Small, *J. Biochem.* 138:781-786 (1986), acetate secretion from *E. coli* under ATP maximization conditions as described in Majewski and Domach, *Biotech. Bioeng.* 35:732-738 (1990) or ethanol secretion by yeast as described in Vanrolleghem et al., *Biotech. Prog.* 12:434-448 (1996). Additionally, this approach can be used to predict or simulate the growth of *E. coli* on a variety of single-carbon sources as well as the metabolism of *H. influenzae* as described in Edwards and Palsson, *Proc. Natl. Acad. Sci.*

97:5528-5533 (2000), Edwards and Palsson, *J. Bio. Chem.* 274:17410-17416 (1999) and Edwards et al., *Nature Biotech.* 19:125-130 (2001).

Given the teachings and guidance provided herein, those skilled in the art will be able to apply various computational frameworks for metabolic modeling and simulation to design and implement biosynthesis of fumaric acid or other desired chemical substrates in host microbial organisms other than *E. coli* and yeast. Such metabolic modeling and simulation methods include, for example, the computational systems exemplified above as SimPheny® and OptKnock.

The non-naturally occurring microbial organisms of the invention can be employed in the integrated process of the invention for growth-coupled production of fumaric acid coupled with transformation to acrylic acid or diesterification followed by transformation to acrylate ester. Essentially any quantity of fumaric acid substrate, including commercial quantities, can be synthesized using the growth-coupled fumaric acid producing microbial organisms of the invention. Because the microbial organisms used in the process of the invention obligatory couple fumaric acid to growth, continuous or near-continuous growth processes are particularly useful for biosynthetic production of fumaric acid. Such continuous and/or near continuous growth processes are exemplified further below. Continuous and/or near-continuous microbial organism growth processes also are well known in the art. Briefly, continuous and/or near-continuous growth processes involve maintaining the microbial organism in an exponential growth or logarythimic phase. Procedures include using apparatuses such as the Evolugator™ evolution machine (Evolugate LLC, Gainesville, Fla.), fermentors and the like. Additionally, shake flask fermentation and growth under microaerobic conditions also can be employed. Given the teachings and guidance provided herein those skilled in the art will understand that the growth-coupled fumaric acid producing microbial organisms can be employed in a variety of different settings under a variety of different conditions using a variety of different processes and/or apparatuses well known in the art.

Generally, the continuous and/or near-continuous production of fumaric acid will include culturing a non-naturally occurring growth-coupled fumaric acid producing organism of the invention in sufficient nutrients and medium to sustain and/or nearly sustain growth in an exponential phase. Continuous culture under such conditions can be grown, for example, for a day, 2, 3, 4, 5, 6 or 7 days or more. Additionally, continuous cultures can include time durations of 1 week, 2, 3, 4 or 5 or more weeks and up to several months. It is to be understood that the continuous and/or near-continuous culture conditions also can include all time intervals in between these exemplary periods.

One particularly useful method for large scale bioproduction of a chemical product is fermentation. Briefly, fermentation procedures are well known in the art. Fermentation of a set of complementary metabolizing organisms in general, and for example, for the biosynthetic production of a target product of the invention such as a chemical compound can be utilized in, for example, batch fermentation, fed-batch fermentation; fed-batch fermentation or continuous fermentation. In addition, any of these methods of fermentation also can be coupled to well know separation methods applicable to fermentation procedures such as batch separation or continuous separation. Exemplary combinations of fermentation and separation methods applicable for bioproduction of a target chemical compound of the invention such as fumaric acid include, for example, batch fermentation and batch separation; batch fermentation and continuous separation; fed-batch fermentation and batch separation; fed-batch fermentation and continuous separation; continuous fermentation and batch separation or continuous fermentation and continuous separation.

Examples of batch and continuous fermentation procedures are well known in the art. An exemplary procedure for fed-batch fermentation and batch separation includes culturing a production organism such as a set of complementary metabolizing organisms in a 10 L bioreactor sparged with an $N_2/CO_2$ mixture, using 5 L broth containing 5 g/L potassium phosphate, 2.5 g/L ammonium chloride, 0.5 g/L magnesium sulfate, and 30 g/L corn steep liquor, and an initial first and second carbon source concentration of 20 g/L. As the CMOs grow and utilize the carbon sources, additional 70% carbon source mixture is fed into the bioreactor at a rate approximately balancing carbon source consumption. The temperature of the bioreactor is generally maintained at 30° C. Growth continues for approximately 24 hours or more, the target chemical compound reaches a concentration of between 20-200 g/L, with the cell density being between about 5 and 10 g/L. Upon completion of the cultivation period, the fermenter contents can be passed through a cell separation unit such as a centrifuge to remove cells and cell debris, and the fermentation broth can be transferred to a product separations unit. Isolation of the target chemical compound can take place by standard separations procedures well known in the art to separate organic products from dilute aqueous solutions, such as liquid-liquid extraction using a water immiscible organic solvent (e.g., toluene) to provide an organic solution of the target chemical compound. The resulting solution can then be subjected to standard distillation methods to remove and recycle the organic solvent and to isolate the target chemical compound having a known boiling point as a purified liquid, for example.

An exemplary procedure for continuous fermentation and continuous separation includes initially culturing a production organism such as a set of complementary metabolizing organisms in batch mode using, for example, a bioreactor apparatus and medium composition exemplified above, except that the initial at least first and second carbon source is about 30-50 g/L. When the carbon source is exhausted, feed medium of the same composition is supplied continuously at a rate of between about 0.5 L/hr and 1 L/hr, and liquid is withdrawn at the same rate. The target chemical compound concentration in the bioreactor generally remains constant at 30-40 g/L, and the cell density generally remains constant at between about 3-5 g/L. Temperature is generally maintained at 30° C., and the pH is generally maintained at about 4.5 using concentrated NaOH and HCl, as required. The bioreactor can be operated continuously, for example, for about one month, with samples taken every day or as needed to assure consistency of the target chemical compound concentration. In continuous mode, fermenter contents are constantly removed as new feed medium is supplied. The exit stream, containing cells, medium, and target chemical compounds or other desired products, can then be subjected to a continuous product separations procedure, with or without removing cells and cell debris, and can be performed by continuous separations methods well known in the art to separate organic products from dilute aqueous solutions and distillation and/or purifications methods such as those exemplified above and well known in the art.

In certain embodiments, the fumaric acid producing organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture.

During or following bioproduction of fumaric acid, a variety of reaction conditions well known in the art can be employed for the cross-metathesis transformation and/or esterification reactions, including diesterification reactions. One particularly useful method for cross-metathesis of fumaric acid to yield two moles of acrylic acid per mole of substrate is exemplified in the Examples below. This method is similarly applicable to the cross-metathesis transformation of fumarate monoesters and fumarate diesters to yield acrylate esters as described previously. This method as well as any of those cross-metathesis reactions exemplified previously can be employed in conjunction with the bioproduction of fumaric acid to integrate the production of the acrylic acid and/or acrylate esters of the invention.

Similarly, any of a variety of esterification reactions also can be employed in the conversion of fumaric acid to fumarate monoester or fumarate diester. A particularly useful esteritication method also is exemplified further below in the Examples. In certain embodiments, fumaric acid produced by culture or fermentation, as exemplified in FIG. 3, can be reacted with alcohols such as ethanol, butanol or any of those described previously to yield the diesters of fumaric acid, which subsequently provide the substrate for cross-metathesis transformation by reaction with ethylene to produce acrylate esters (see, for example, FIG. 2). Formation of fumarate diesters can facilitate separation from the aqueous culture medium or fermentation broth and thereby facilitate metathesis transformation and subsequent isolation of pure acrylate ester product. In an embodiment described further below where the biological production of substrate is derived from renewable feedstocks, production of alcohols such as ethanol and butanol also can be generated by microbial organisms from renewable feedstocks. Further integration of alcohol bioproduction from renewable feedstocks can result in all but one carbon of the acrylate esters of the invention being derived from non-depletive sources.

Integration of cross-metathesis and/or esterification can be performed using a variety of process configurations. For example, cross-metathesis transformation can be performed directly in the culture medium and/or fermentation broth. In this embodiment, cross-metathesis and/or esterification regents can be added directly to the medium or broth in concentrations sufficient to catalyze transformation or esterification of fumaric acid to acrylic acid or acrylate ester. Similarly, following esterification or diesterification, esterification reagents can optionally be removed or neutralized and cross-metathesis reagents can be added to the medium or broth in concentrations sufficient to catalyze the transformation of fumarate monoester or fumarate diester to yield an acrylic acid/acrylate ester mixture or to yield acrylate ester.

In a further embodiment, cross-metathesis and/or esterification reactions also can be performed following any of a variety of treatments to the culture medium and/or fermentation broth. For example, the medium or broth can be treated to adjust the pH, temperature and/or other characteristics to a desired level prior to or simultaneously with addition cross-metathesis and/or esterification reagents. Cells or other particulate matter can be removed or partially removed prior to addition of synthesis reagents by, for example, sedimentation, filtration, centrifugation or other method well known in the art. Polypeptides and/or other soluble macromolecules in the medium and/or broth can be removed by, for example, precipitation, size exclusion chromatography, ion exchange chromatography or other methods well known in the art. The medium or broth also can be exchanged or partially exchanged with a desired solution, buffer or reaction formulation suitable or optimal for cross-metathesis transformation and/or esterification. Given the teachings and guidance provided herein, those skilled in the art will know, or can determine, suitable conditions for coupling cross-metathesis transformation and/or esterification directly in a culture medium or fermentation broth of fumaric acid producing cells. For example, streamlined production of acrylic acid or acrylate esters can be achieved by coupling the bioproduction and chemical synthesis steps with little to no manipulations of the medium or broth. Yields of acrylic acid or acrylate ester can be optimized by employing some or all of the above process configurations in conjunction with or prior to cross-metathesis or esterification reactions.

In an alternative embodiment, fumaric acid can be harvested or isolated at any time point during culture or during the continuous and/or near-continuous culture period exemplified above and then subjected to cross-metathesis transformation or diesterification followed by cross-metathesis transformation to produce acrylic acid and acrylate ester respectively. Those skilled in the art will understand that the longer the microbial organisms are maintained in a continuous and/or near-continuous growth phase, the proportionally greater amount of fumaric acid can be produced. A variety of purification methods for acrylic acid or acrylate esters are well known in the art. Any of such methods can be used for isolation and/or purification of acrylic acid or acrylate ester of the invention.

Therefore, the invention also provides a process for producing an acrylate ester. The process includes: (a) culturing in a sufficient amount of nutrients and media a non-naturally occurring microbial organism having a set of metabolic modifications obligatorily coupling fumaric acid production to growth of the microbial organism, the set of metabolic modifications includes disruption of at least one of the gene sets having: (1) fumABC, zwf, purU, or (2) fumABC, zwf, glyA, or an ortholog thereof, to produce stable growth-coupled production of fumaric acid; (b) performing diesterification of the fumaric acid to produce fumarate diester, and (c) contacting the fumarate diester with a sufficient amount of ethylene in the presence of a cross-metathesis catalyst to produce about two moles of an acrylate ester per mole of fumarate diester.

In addition to producing acrylic acid and/or acrylate esters as exemplified in FIG. 3 using glucose as a carbon source for glycolysis, the integrated process of the invention also can be employed to produce these products from renewable feedstocks. Many different carbon substrates, such as glucose, sucrose, xylose, arabinose, sorbitol, sucrose, glycerol or synthesis gas (a mixture carbon monoxide, hydrogen and carbon dioxide), can be derived from renewable feedstocks and thereby serve as energy sources for a culture or fermentation process. These and other substrates known in the art can be used for biological production of fumaric acid.

In some embodiments of the invention, carbon sources for biological growth and metabolism can be derived from a variety of different biomasses. Given the teachings and guidance provided herein, those skilled in the art will understand that a fumaric acid or other fumaric acid substrate producing bioprocess of the invention can encompass the use of a wide range of different carbon sources. Therefore, the bioproduction of substrate such as fumaric acid and/or an alcohol is applicable for use with a wide range of different carbon sources and/or carbon source mixtures including, for example, biomass and renewable feedstocks.

Carbon sources useful for bioproduction of a substrate such as fumaric acid include, for example, sugars or mixtures of sugars or other energy sources in growth media, fermentation broth or the like. For example, a fumaric acid substrate producing bioprocess of the invention can be generated where the fumaric acid producing microbial organisms grow on single or multiple carbon sources such as on glucose or both on glucose and arabinose, for example. A culture media can be obtained, produced or supplemented to contain either or both of these sugars as well as other sugars or carbon sources known in the art. Alternatively, heterogeneous mixtures having or capable of generating the requisite mixtures of energy sources also can be used as substrate mixture. A particular example of such a heterogeneous mixture includes a feedstock including, for example, renewable feedstocks and/or renewable feedstocks derived from biomass. Therefore, carbon source mixtures can include growth media, fermentation broth and/or complex feedstocks having more than one different energy source can be used for culture or fermentation of the microbial organisms of the invention. Other sources of carbon well known in the art also can be utilized with bioprocess of the invention.

Energy sources within a simple or complex mixture include, for example, carbohydrate, protein, lipid, fat and other macromolecules or chemical compounds applicable for conversion by cellular biochemical processes. Such energy sources typically supply the requisite carbon source for energy production used in biochemical process. Exemplary carbohydrates include, for example, simple and complex carbohydrates such as monosaccharides such as sugars and polysaccharides such as starches, respectively. Exemplary proteins include, for example, all types of polypeptides, including proteoglycans. These exemplary macromolecules as well as lipids, fats and other macromolecules are well known in the art and are all available as energy sources for the sets of complementary metabolizing organisms of the invention.

Exemplary materials and/or substances supplying these energy sources within complex mixtures such as biomass and/or renewable feedstocks include, for example, those described previously as well as other renewable resources or byproducts well known to those skilled in the art. For example, biomass can provide a wide variety of energy sources including the above carbohydrate, protein, lipid, fat as well as other molecules such as aromatic compounds and/or proteineaceous substances such as lignin. Biomass and renewable feedstocks are particularly useful as sources of a variety of carbohydrate. Such sources include, for example, cellulosic biomass, a hemicellulosic biomass, wheat straw, corn stover, reed canary grass, starch, corn, wheat or cotton woodchips starch, corn, wheat, cotton. Portions, chaff, fractions and waste products, for example, of these exemplary biomasses and renewable feedstocks as well as others well known in the art also are particularly useful sources for a variety of carbohydrates that can be used in a growth medium for a set of complementary metabolizing organisms of the invention. Particularly useful carbon sources include medium or feedstocks containing different simple or complex carbohydrates. Carbohydrates provide an efficient carbon source for cellular proliferation. Exemplary carbohydrates include the sugars glucose, sucrose, xylose, arabinose, galactose, mannose or fructose.

Feedstocks containing the sugar energy sources exemplified above or other carbon sources useful for growth of the complementary metabolizing organisms of the invention include, for example, cellulosic biomass, hemicellulosic biomass and lignin feedstocks. Such biomass feedstocks contain, for example, carbohydrate substrates useful as carbon sources such as glucose, sucrose, xylose, arabinose, galactose, mannose, fructose and starch.

In other embodiments, hydrolysis of biomass can generate toxic compounds which also can be beneficially utilized from the substrate media as carbon sources for bioprocessing. Exemplary toxic compounds that can be harnessed as carbon or other fuel sources include furfurals, aromatics, acetate and other undetermined substrates. Removal of these toxic compounds also is particularly useful to the overall cost effectiveness of the process because it eliminates requirements for implementation of separate unit operations prior to, for example, the actual bioconversion step. When used as a carbon source, toxic compounds can be consumed, for example, before the main bioconversion takes place or concurrently in the same reaction vessel. One specific embodiment, achieves toxic product removal by conversion into cell matter or other products of interest.

Briefly, microbial organisms can be designed and generated to utilize one or more byproducts, including toxic byproducts, generated during co-culture of the complementary metabolizing organisms. For example, a substrate producing microbial organism also can be modified to metabolize a byproduct of the culture or fermentation itself. In this specific embodiment, the initial carbon source contained in a medium supporting growth and metabolism produces a renewable energy source that is further utilized by, for example, the modified organism.

Any of the integrated processes of the invention described above can be configured as a production system useful for the manufacture of acrylic acid and/or acrylate esters. The amounts of acrylic acid or acrylate ester that can be manufactured can range from small, research quantities to large commercial-scale amounts. In the former, those skilled in the art will understand that small cultures of fumaric acid producing organisms can be useful for ease of handling and efficiency. In the latter, those skilled in the art will understand that fermentation-size cultures of fumaric acid producing organisms can be useful to efficiently achieve desired productivity levels.

A production system of the invention can be configured in a variety of different ways. For example, a production system can contain some or all of the components needed to generate fumaric acid, acrylic acid and/or acrylate ester. In the specific embodiment where the production system contains all of the components, the fumaric acid producing cells can be in stationary or log growth phase. A production system also can contain less than all components and be poised for cell growth, fumaric acid production, acrylic acid production and/or acrylate ester production by the addition of one or more components of the previously described integrated process of the invention.

Therefore, the invention further provides acrylic acid production system. The production system includes: (a) a culture of a non-naturally occurring microbial organism having a set of metabolic modifications obligatorily coupling fumaric acid production to growth of the microbial organism, the set of metabolic modifications includes disruption of at least one of the gene sets having: (1) fumABC, zwf, purU, or (2) fumABC, zwf, glyA, or an ortholog thereof, which confer stable growth-coupled production of fumaric acid, and (b) an amount of ethylene and a cross-metathesis transformation catalyst sufficient to produce about two moles of acrylic acid per mole of fumaric acid.

An acrylate ester production system is also provided. The production system includes: (a) a culture of a non-naturally occurring microbial organism having a set of metabolic modifications obligatorily coupling fumaric acid production to growth of the microbial organism, the set of metabolic modifications includes disruption of at least one of the gene sets having: (1) fumABC, zwf, purU, or (2) fumABC, zwf, glyA or an ortholog thereof, which confer stable growth-coupled production of fumaric acid; (b) at least one diesterification reagent sufficient to produce fumarate diester from the fumaric acid, and (c) an amount of ethylene and a cross-metathesis catalyst sufficient to produce about two moles of an acrylate ester per mole of fumarate diester.

It is understood that modifications which do not substantially affect the activity of the various embodiments of this invention are also included within the definition of the invention provided herein. Accordingly, the following examples are intended to illustrate but not limit the present invention.

Example I

This Example describes chemical synthesis methods for cross-metathesis of fumaric acid to acrylic acid and esters thereof and for the diesterification of fumaric acid to fumarate diester.

Acrylic acid from fumaric acid and ethylene: Briefly, a 1 L glass reactor composed of thick wall glass is charged under nitrogen or argon with an appropriate solvent such as dichloromethane or dichloroethane (500 mL), fumaric acid (100 g, 0.86 mol), and the Grubbs Ruthenium metathesis catalyst (1.0-0.01 mol %). After stirring for 10-60 min under nitrogen, the vessel is pressurized with 1.0-5.0 atm of ethylene gas and the reaction is stirred at 0-50° C. over a period of up to 24 hours or until process monitoring indicates the reaction is complete. The unused ethylene is then removed and recovered and the reaction vessel is opened to the atmosphere. The solution is treated with aqueous sodium hydroxide (300-500 mL, 1-5 M solution) and the aqueous layer is extracted twice with the above solvent. The aqueous layer is then acidified to pH 0-2 and extracted with dichloromethane or diethylether (5×100 mL). Following removal of the solvent, hydroquinone is added to limit polymerization, and the crude acrylic acid is purified by distillation (b.p. 139-140° C.).

Dialkyl esters of fumaric acid: Dialkylfumarate esters or the diesters of fumaric acid (e.g., dimethyl and dibutyl fumarate) are readily available from many commercial sources or are prepared by various routes including diesterification of fumaric acid with aliphatic alcohols in the presence of a p-toluene sulfonic acid catalyst. Alternatively, the esters can be prepared from fumaryl chloride and alkyl alcohols using an amine catalyst. A representative example is provided below.

Fisher Synthesis of Dialkyl Fumarate Esters is performed as described in, for example, U.S. patent application 20020040123 A1. Briefly, monomer synthesis from fumaric acid and 1-eicosanol is performed by adding into the reaction flask (equipped with a condenser and a Dean-Stark trap apparatus to remove the reaction water as it formed), 2.8 g (FW 116.07, 0.01875 moles) of fumaric acid, 11.2 g (0.0375 moles) of 1-eicosanol (FW 298.56), 0.3567 g (0.00188 mole) of .rho.-toluenesulfonic acid monohydrate, and 50 mL to toluene. The mixture was heated at 130.degree. C. for 18 hours under nitrogen. The reaction was then cooled to room temperature and filtered and solvent toluene was removed by a rotary evaporator to obtain the product (mp 71-73.degree. C.). The C.sub.20 fumarate ester product was characterized by IR and NMR spectroscopy. The IR spectrum of the product was recorded as the melted solid film in NaCl plates. The spectrum showed an ester peak at 1728 cm.sup.−1 and a double bond absorption peak at 1647 cm.sup.−1. .sup.13C NMR of the product showed the double bond absorption peak at 134.0 ppm (trans —HC.dbd.CH—, carbon) and the carbonyl ester peak at 165 ppm. The NMR spectrum also showed an absorption peak at 66 ppm due to a methylene next to ester functionality (—C(O)O—CH.sub.2-). The absorption peaks in the aliphatic region are typical of the straight chain alkyl groups.

Alkyl acrylate esters from dialkyl fumarate and ethylene: The same general protocol is employed as described above with the reaction vessel being charged with dialkyl fumarate rather than fumaric acid. The final mixture following completion of the reaction would be processed by crystallization or distillation to obtain the purified alkyl acrylate.

Example II

This Example describes the combined biosynthesis and chemical of acrylic acid.

Acrylic Acid from biologically produced fumaric acid: Acrylic acid will be produced by reaction between fumaric acid produced by fermentation and ethylene in the presence of a suitable catalyst (e.g., Grubbs catalyst). In this case, a fermentation process is implemented using an organism engineered for high level production of fumaric acid. Performing the metathesis process directly on the fermentation broth following completion of the fermentation process is the preferred process. A general procedure for the combined fermentation and metathesis process is as follows:

The production organism is grown in a 10 L bioreactor sparged with an N2/CO2 mixture, using 5 L broth containing 5 g/L potassium phosphate, 2.5 g/L ammonium chloride, 0.5 g/L magnesium sulfate, and 30 g/L corn steep liquor, and an initial glucose concentration of 20 g/L. As the cells grow and utilize the glucose, additional 70% glucose is fed into the bioreactor at a rate approximately balancing glucose consumption. The temperature of the bioreactor is maintained at 30 degrees C. Growth continues for approximately 24 hours, until fumaric acid reaches a concentration of between 10-200 g/L, with the cell density being between 5 and 50 g/L. Upon completion of the cultivation period, the fermenter contents are passed through a cell separation unit (e.g., centrifuge) to remove cells and cell debris, and the fermentation broth is transferred to a secondary reaction unit where Grubbs catalyst (1.0-0.01 mol %) is added to the broth, possibly along with an appropriate organic solvent to increase catalyst solubility, and the reactor is pressurized with ethylene (1.0-5.0 atm). After stirring the time required for complete reaction, ethylene pressure is released and recovered, and acrylic acid is separated from the broth and purified as described above.

Example III

This example demonstrates the conversion of diethylfumarate to ethyl acrylate.

Example of metathesis of fumarate: In order to demonstrate the feasibility of converting fumarate(s) to acrylate(s) through the addition of ethylene, a series of commercially available metathesis catalysts were screened. The following results demonstrate the ability of the metathesis reaction to take place and suggest areas to explore for enhanced performance.

General:

Experiments were conducted in 150-mL Fisher-Porter pressure bottles at 150 psi. Compressed ethylene (99.95%) was purchased from Praxair and used as received. All solvents and chemicals were purchased from Aldrich Chemicals. Diethyl fumarate (98%) was distilled before use. Diethyl maleate, dimethyl fumarate, ethyl acrylate, and acrylic acid were used as received. All catalysts were prepared by Materia, Inc. and obtained from either Materia or Aldrich Chemicals. All Gas Chromatography (GC) data were acquired with Agilent Technologies 6850 Series II using the HP-5 column of J&W Scientific. The temperature profile was held at 100° C. for 1 minute, ramped up to 250° C. with the rate of 10° C. per minute, and held at 250° C. for 5 minutes. Nuclear magnetic resonance (NMR) data was obtained from the Varian 400 MHz instrument. NMR solvents were purchased from Cambridge Isotope Inc.

Standard Procedure: Substrate (e.g., diethylfumarate, 5 g), catalyst (2.5 mol %) and magnetic stirring bar were added to a Fisher-Porter bottle inside a nitrogen-filled glove box. The Fisher-Porter bottle was assembled and the apparatus was moved out of the box and connected to an ethylene cylinder. The ethylene line was purged with ethylene for a several minutes and the Fisher-Porter bottle was then pressurized with ethylene to the desired level (150 psi). The bottle was placed into an oil bath at 60° C. on the hot plate of a magnetic stirrer. After the indicated reaction time, the bottle was removed from the oil bath and cooled to room temperature in air. The pressure was released and the contents were filtered through filter paper. An aliquot was diluted in dichloromethane or chlorobenzene in a GC vial and the sample was analyzed by GC for percent conversion of diethyl fumarate to ethyl acrylate.

The catalysts screened in this experiment included five commercially available catalysts. All catalysts can be obtained from Materia or from Sigma-Aldrich. Full details on these five catalysts are provided in the Table 4 below.

TABLE 4

List of commercially available catalysts screened (Table taken from the Materia, Inc. product catalog located on the world wide web at materia-inc.com)

| Chemical Structure | Product & CAS# | Product Description | | | Sigma-Aldrich Product# |
|---|---|---|---|---|---|
| [structure] | C627 [301224-40-8] | Hoveyda-Grubbs Second Generation Catalyst $C_{31}H_{38}Cl_2N_2ORu$ Ruthenium, [1,3-bis(2,4,6-trimethyl-phenyl)-2-imidazolidinylidene] dichloro[[2-(1-methylethoxy)phenyl] methylene] | FW | 626.62 | 569755 |
| [structure] | C793 [927429-60-5] | $C_{42}H_{57}Cl_2N_2PRu$ [1,3-Bis(2-methylphenyl)-2-imidazolidinylidene]dichloro(benzylidene) (tricyclohexylphosphine)ruthenium(II) | FW | 792.87 | 682284 |
| [structure] | C823 [172222-30-9] | Grubbs First Generation Catalyst $C_{43}H_{72}Cl_2P_2Ru$ Ruthenium, dichloro(phenylmethylene)bis (tricyclohexylphosphine) | FW | 822.95 | 579726 |
| [structure] | C827 [253688-91-4] | $C_{44}H_{67}Cl_2N_2PRu$ [1,3-Bis(2,4,6-trimethylphenyl)-2-imidazolidinylidene]dichloro(3-methyl-2-butenylidene) (tricyclohexyl-phosphine)ruthenium(II) | FW | 826.97 | 682365 |
| [structure] | C848 [246047-72-3] | Grubbs Second Generation Catalyst $C_{46}H_{65}Cl_2N_2PRu$ Ruthenium, [1,3-bis-(2,4,6-trimethyl-phenyl)-2-imidazolidinylidene]dichloro (phenylmethylene) (tricyclohexyl-phosphine) | FW | 848.97 | 569747 |

Figure 4:
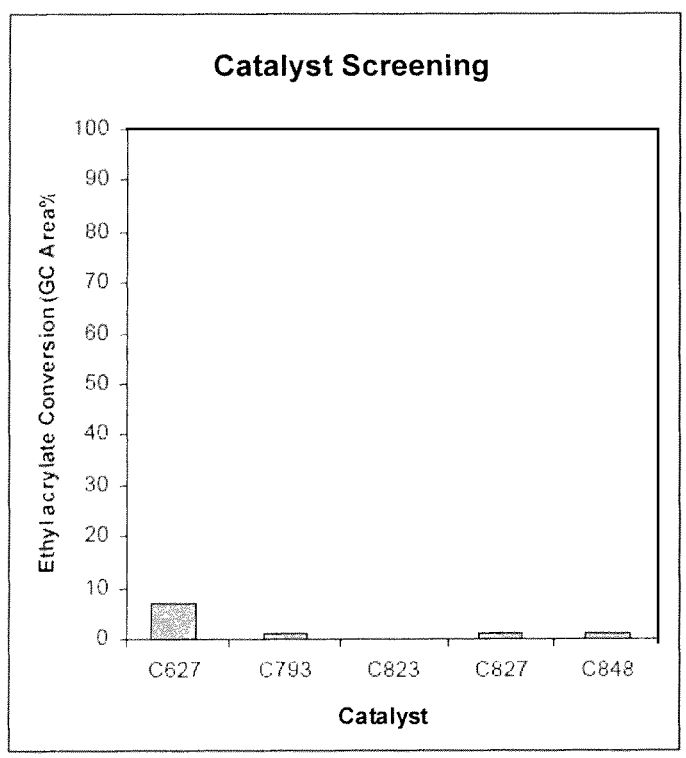
FIG. 4 is a bar graph showing the yield of ethyl acrylate as a function metathesis catalyst.

Screening the catalysts shown in Table 4 under the experimental conditions described above yielded results demonstrating the conversion of the fumarate(s) into acrylate(s). The results for diethyl fumarate are shown in the Table 5 below and in FIG. 4. These reactions were performed with neat substrate and no additional solvent. The reactions generally proceeded in a sluggish manner, especially with Generation 1 and 2 Grubbs catalysts, where no conversion (C823) and 1% conversion (C848) were observed, respectively. The best conversion and yield of 7% was seen with catalyst C627, which is the only phosphine-free system tested. Similar results were achieved with dimethyl fumarate.

TABLE 5

Results of catalyst screening (EA: ethyl acrylate, DEF: diethyl fumarate; IE: itaconic acid diethyl ester)

| Catalyst | Cat (mol %) | C2H4 (psi) | T (C) | t (h) | Composition(Area %) | | |
|---|---|---|---|---|---|---|---|
| | | | | | EA | DEF | IE |
| C627 | 2.5 | 150 | 60 | 4 | 7 | 88 | 4 |
| C793 | 2.5 | 150 | 60 | 4 | 1 | 96 | 0 |
| C823 | 2.5 | 150 | 60 | 16 | 0 | 93 | 0 |
| C827 | 2.5 | 150 | 60 | 16 | 1 | 93 | 0 |
| C848 | 2.5 | 150 | 60 | 4 | 1 | 93 | 0 |

Example IV

This example demonstrates the biosynthesis of fumaric acid.

Example of biosynthesis of fumaric acid: *Escherichia coli* K-12 MG1655 served as the wild-type strain into which the deletions are introduced. Deletions of *E. coli* genes fumABC, zwf, and purU was performed by using the well-known Red E/T technology. The strains were constructed by incorporating in-frame deletions using homologous recombination via the λ Red recombinase system of Datsenko and Wanner. The approach involved replacing a chromosomal sequence (i.e., the gene targeted for removal) with a selectable antibiotic resistance gene, which itself was later removed. No drug resistance markers remained after each deletion, allowing accumulation of multiple mutations in each target strain.

Production of fumarate. Wild type *E. coli*, strain 1 (ΔfumABC, Δzwf) and strain 2 (ΔfumABC, Δzwf; ΔpurU) were tested in shake flask cultures before subjecting them to adaptive evolution. Cultures were grown aerobically in M9 minimal medium containing 2 g/L glucose, and concentrations of glucose, fumarate, and other organic acid products in the culture supernatant were determined by HPLC using an HPX-87H column (BioRad). While the wild-type *E. coli* MG1655 did not secrete any fumarate, strain 1 secreted 0.1 mol fumarate per mol of glucose consumed over 48 h. No other byproducts were detected from the HPLC measurements. Quite surprisingly, strain 2 that has an additional deletion in purU formed slightly more fumarate (0.125±0.014 mol/mol glucose consumed) and a lot of acetate (0.90 mol/mol glucose consumed).

After briefly evolving strain 2 in chemostat for 8 days, it was observed that the growth rate improved for 0.38 per hour to 0.48 per hour. This is in reasonable agreement with the growth rate of 0.58 per hour predicted by our models. However, the measured fumarate yield did not significantly increase in shake flask cultures,

TABLE 1

Reaction combinations targeted for removal to enhance succinate production in *E. coli*.

| | |
|---|---|
| 1. | FUM |
| 2. | FUM MTHFC PGDH |
| 3. | FUM MTHFC PGL |
| 4. | FTHFD FUM G6PDHy |
| 5. | FUM G6PDHy MTHFC |
| 6. | FTHFD FUM PGL |
| 7. | FUM G6PDHy GLYCL |
| 8. | FUM GLYCL PGDH |
| 9. | FUM GLYCL PGL |
| 10. | FTHFD FUM TKT1 |
| 11. | FUM MTHFC TKT1 |
| 12. | FUM MTHFC TAL |
| 13. | FTHFD FUM TAL |
| 14. | FUM GLYCL TKT1 |
| 15. | FUM GLYCL TAL |
| 16. | FUM MTHFC RPE |
| 17. | FTHFD FUM RPE |
| 18. | FUM GLYCL RPE |
| 19. | FUM MTHFC TKT2 |
| 20. | FTHFD FUM TKT2 |
| 21. | FUM GLYCL TKT2 |
| 22. | MDH ME1x ME2 |
| 23. | GLYCL NADH6 PGI |
| 24. | FUM G6PDHy GLUDy MTHFC |
| 25. | FTHFD FUM G6PDHy GLUDy |
| 26. | FDH2 FUM GLUDy PGL |
| 27. | FUM GLUDy MTHFC PGDH |
| 28. | FDH2 FUM G6PDHy GLUDy |
| 29. | FDH2 FUM GLUDy PGDH |
| 30. | FUM GLUDy MTHFC PGL |
| 31. | FTHFD FUM GLUDy PGL |
| 32. | FUM GLUDy GLYCL PGDH |
| 33. | FUM G6PDHy GLUDy GLYCL |
| 34. | FUM GLUDy GLYCL PGL |
| 35. | FDH2 FUM GLUDy TKT1 |
| 36. | FDH2 FUM GLUDy TAL |
| 37. | FTHFD FUM GLUDy TAL |
| 38. | FTHFD FUM GLUDy TKT1 |
| 39. | FUM GLUDy MTHFC TKT1 |
| 40. | FUM GLUDy MTHFC TAL |
| 41. | FUM GLUDy GLYCL TKT1 |
| 42. | FUM GLUDy GLYCL TAL |
| 43. | FUM G6PDHy MTHFC THD2 |
| 44. | FUM MTHFC PGL THD2 |
| 45. | FUM MTHFC PGDH THD2 |
| 46. | FTHFD FUM G6PDHy THD2 |
| 47. | FTHFD FUM PGL THD2 |
| 48. | FUM GLYCL PGDH THD2 |
| 49. | FUM G6PDHy GLYCL THD2 |
| 50. | FUM GLYCL PGL THD2 |
| Si. | FDH2 FUM GLUDy RPE |
| 52. | FUM GLUDy MTHFC RPE |
| 53. | FTHFD FUM GLUDy RPE |
| 54. | FUM GLUDy GLYCL RPE |
| 55. | FUM MTHFC PDH PGDH |
| 56. | FTHFD FUM PDH PGL |
| 57. | FTHFD FUM G6PDHy PDH |
| 58. | FUM MTHFC PDH PGL |
| 59. | FTHFD FUM PDH PGDH |
| 60. | FUM G6PDHy MTHFC PDH |
| 61. | FUM GLYCL PDH PGDH |
| 62. | FUM GLYCL PDH PGL |
| 63. | FUM G6PDHy GLYCL PDH |
| 64. | FUM GLCpts MTHFC PGDH |
| 65. | FUM G6PDHy GLCpts MTHFC |
| 66. | FTHFD FUM G6PDHy GLCpts |
| 67. | FTHFD FUM GLCpts PGL |
| 68. | FTHFD FUM GLCpts PGDH |
| 69. | FUM GLCpts MTHFC PGL |
| 70. | FUM GLCpts GLYCL PGDH |
| 71. | FUM G6PDHy GLCpts GLYCL |
| 72. | FUM GLCpts GLYCL PGL |
| 73. | FDH2 FUM GLUDy TKT2 |
| 74. | FTHFD FUM GLUDy TKT2 |
| 75. | FUM GLUDy MTHFC TKT2 |
| 76. | FUM GLUDy GLYCL TKT2 |
| 77. | FUM MTHFC TAL THD2 |

TABLE 1-continued

Reaction combinations targeted for removal to enhance succinate production in *E. coli*..

| | |
|---|---|
| 78. | FUM MTHFC THD2 TKT1 |
| 79. | FTHFD FUM TAL THD2 |
| 80. | FTHFD FUM THD2 TKT1 |
| 81. | FUM GLYCL TAL THD2 |
| 82. | FUM GLYCL THD2 TKT1 |
| 83. | FTHFD FUM PDH TKT1 |
| 84. | FTHFD FUM PDH TAL |
| 85. | FUM MTHFC PDH TAL |
| 86. | FUM MTHFC PDH TKT1 |
| 87. | FUM GLYCL PDH TAL |
| 88. | FUM GLYCL PDH TKT1 |
| 89. | FUM GLCpts MTHFC TAL |
| 90. | FTHFD FUM GLCpts TKT1 |
| 91. | FTHFD FUM GLCpts TAL |
| 92. | FUM GLCpts MTHFC TKT1 |
| 93. | FUM GLCpts GLYCL TAL |
| 94. | FUM GLCpts GLYCL TKT1 |
| 95. | CBMK2 FTHFD FUM PGDH |
| 96. | CBMK2 FUM MTHFC PGL |
| 97. | CBMK2 FUM MTHFC PGDH |
| 98. | CBMK2 FUM G6PDHy MTHFC |
| 99. | CBMK2 FTHFD FUM PGL |
| 100. | CBMK2 FTHFD FUM G6PDHy |
| 101. | FTHFD FUM RPE THD2 |
| 102. | FUM MTHFC RPE THD2 |
| 103. | CBMK2 FUM G6PDHy GLYCL |
| 104. | CBMK2 FUM GLYCL PGL |
| 105. | CBMK2 FUM GLYCL PGDH |
| 106. | FUM GLYCL RPE THD2 |
| 107. | FUM G6PDHy GLU5K MTHFC |
| 108. | FUM G5SD MTHFC PGDH |
| 109. | FUM G5SD MTHFC PGL |
| 110. | FUM G5SD G6PDHy MTHFC |
| 111. | FTHFD FUM G5SD PGL |
| 112. | FUM GLU5K MTHFC PGL |
| 113. | FTHFD FUM G5SD PGDH |
| 114. | FTHFD FUM GLU5K PGL |
| 115. | FTHFD FUM G5SD G6PDHy |
| 116. | FTHFD FUM GLU5K PGDH |
| 117. | FTHFD FUM G6PDHy GLU5K |
| 118. | FUM GLU5K MTHFC PGDH |
| 119. | ASNS2 FUM G6PDHy MTHFC |
| 120. | ASNS2 FTHFD FUM PGL |
| 121. | ASNS2 FUM MTHFC PGL |
| 122. | ASNS2 FTHFD FUM PGDH |
| 123. | ASNS2 FUM MTHFC PGDH |
| 124. | ASNS2 FTHFD FUM G6PDHy |
| 125. | FUM GLU5K GLYCL PGDH |
| 126. | FUM G5SD GLYCL PGL |
| 127. | FUM G5SD G6PDHy GLYCL |
| 128. | FUM GLU5K GLYCL PGL |
| 129. | FUM G5SD GLYCL PGDH |
| 130. | FUM G6PDHy GLU5K GLYCL |
| 131. | ASNS2 FUM GLYCL PGL |
| 132. | ASNS2 FUM G6PDHy GLYCL |
| 133. | ASNS2 FUM GLYCL PGDH |
| 134. | FDH2 FORt FUM PGDH |
| 135. | FDH2 FORt FUM PGL |
| 136. | FDH2 FORt FUM G6PDHy |
| 137. | FUM MTHFC PDH RPE |
| 138. | FTHFD FUM PDH RPE |
| 139. | FUM GLYCL PDH RPE |
| 140. | FUM GLCpts MTHFC RPE |
| 141. | FTHFD FUM GLCpts RPE |
| 142. | FUM GLCpts GLYCL RPE |
| 143. | CBMK2 FUM MTHFC TKT1 |
| 144. | CBMK2 FTHFD FUM TAL |
| 145. | CBMK2 FTHFD FUM TKT1 |
| 146. | CBMK2 FUM MTHFC TAL |
| 147. | CBMK2 FUM GLYCL TAL |
| 148. | CBMK2 FUM GLYCL TKT1 |
| 149. | FTHFD FUM THD2 TKT2 |
| 150. | FUM MTHFC THD2 TKT2 |
| 151. | FUM G5SD MTHFC TKT1 |
| 152. | FTHFD FUM G5SD TKT1 |
| 153. | FTHFD FUM G5SD TAL |
| 154. | FTHFD FUM GLU5K TKT1 |
| 155. | FUM GLU5K MTHFC TAL |
| 156. | FTHFD FUM GLU5K TAL |
| 157. | FUM G5SD MTHFC TAL |
| 158. | FUM GLU5K MTHFC TKT1 |
| 159. | ASNS2 FTHFD FUM TKT1 |
| 160. | ASNS2 FUM MTHFC TAL |
| 161. | ASNS2 FTHFD FUM TAL |
| 162. | ASNS2 FUM MTHFC TKT1 |
| 163. | FUM GLYCL THD2 TKT2 |
| 164. | FUM GLU5K GLYCL TKT1 |
| 165. | FUM G5SD GLYCL TKT1 |
| 166. | FUM GLU5K GLYCL TAL |
| 167. | FUM G5SD GLYCL TAL |
| 168. | ASNS2 FUM GLYCL TKT1 |
| 169. | ASNS2 FUM GLYCL TAL |
| 170. | FTHFD FUM PDH TKT2 |
| 171. | FUM MTHFC PDH TKT2 |
| 172. | FDH2 FORt FUM TAL |
| 173. | FDH2 FORt FUM TKT1 |
| 174. | FUM GLYCL PDH TKT2 |
| 175. | FTHFD FUM GLCpts TKT2 |
| 176. | FUM GLCpts MTHFC TKT2 |
| 177. | FUM GLCpts GLYCL TKT2 |
| 178. | CBMK2 FUM MTHFC RPE |
| 179. | CBMK2 FTHFD FUM RPE |
| 180. | CBMK2 FUM GLYCL RPE |
| 181. | FUM GLU5K MTHFC RPE |
| 182. | FUM G5SD MTHFC RPE |
| 183. | FTHFD FUM GLU5K RPE |
| 184. | FTHFD FUM G5SD RPE |
| 185. | ASNS2 FUM MTHFC RPE |
| 186. | ASNS2 FTHFD FUM RPE |
| 187. | FUM G5SD GLYCL RPE |
| 188. | FUM GLU5K GLYCL RPE |
| 189. | ASNS2 FUM GLYCL RPE |
| 190. | FDH2 FORt FUM RPE |
| 191. | CBMK2 FTHFD FUM TKT2 |
| 192. | CBMK2 FUM MTHFC TKT2 |
| 193. | CBMK2 FUM GLYCL TKT2 |
| 194. | FUM GLU5K MTHFC TKT2 |
| 195. | FTHFD FUM G5SD TKT2 |
| 196. | FTHFD FUM GLU5K TKT2 |
| 197. | FUM G5SD MTHFC TKT2 |
| 198. | ASNS2 FUM MTHFC TKT2 |
| 199. | ASNS2 FTHFD FUM TKT2 |
| 200. | FUM GLU5K GLYCL TKT2 |
| 201. | FUM G5SD GLYCL TKT2 |
| 202. | ASNS2 FUM GLYCL TKT2 |
| 203. | FDH2 FORt FUM TKT2 |
| 204. | ACt6 FUM MTHFC THD5 |
| 205. | ACt6 FDH2 FUM THD5 |
| 206. | ACt6 FTHFD FUM THD5 |
| 207. | ACt6 FUM GLYCL THD5 |
| 208. | FDH2 FUM PTAr THD5 |
| 209. | FUM HEX1 PGI PPS |
| 210. | ACKr FTHFD FUM THD5 |
| 211. | ACKr FDH2 FUM THD5 |
| 212. | FTHFD FUM PTAr THD5 |
| 213. | FUM GLCt2 PGI PPS |
| 214. | FUM MTHFC PTAr THD5 |
| 215. | ACKr FUM MTHFC THD5 |
| 216. | FUM GLYCL PTAr THD5 |
| 217. | ACKr FUM GLYCL THD5 |
| 218. | ACt6 FUM HEX1 PPS |
| 219. | ACt6 FUM GLCt2 PPS |
| 220. | FUM HEX1 PPS PTAr |
| 221. | FUM GLCt2 PPS PTAr |
| 222. | ACKr FUM HEX1 PPS |
| 223. | ACKr FUM GLCt2 PPS |
| 224. | FUM MTHFC PDH PGI |
| 225. | FTHFD FUM PDH PGI |
| 226. | FUM GLYCL PDH PGI |
| 227. | ACt6 FUM MTHFC PGI |
| 228. | ACt6 FTHFD FUM PGI |
| 229. | ACt6 FUM GLYCL PGI |
| 230. | MDH ME1x ME2 SUCOAS |
| 231. | FUM MTHFC PGI PTAr |

TABLE 1-continued

Reaction combinations targeted for removal to enhance succinate production in *E. coli*.

| | |
|---|---|
| 232. | FTHFD FUM PGI PTAr |
| 233. | ACKr FTHFD FUM PGI |
| 234. | FUM GLYCL PGI PTAr |
| 235. | ACKr FUM MTHFC PGI |
| 236. | HEX1 MDH PGI PPS |
| 237. | ACKr FUM GLYCL PGI |
| 238. | GLCt2 MDH PGI PPS |
| 239. | PDH PGDH PPS THD2 |
| 240. | FUM MTHFC PGL PGM THD2 |
| 241. | ENO FUM G6PDHy MTHFC THD2 |
| 242. | ENO FTHFD FUM PGL THD2 |
| 243. | ENO FTHFD FUM G6PDHy THD2 |
| 244. | ENO FUM MTHFC PGL THD2 |

TABLE 2

A list of all the reaction stoichiometries and the associated genes known to be associated with the reactions identified for deletion in the strategies listed in Table 1.

| Reaction Abbreviation | Reaction Stoichiometry | Associated genes |
|---|---|---|
| ACKr | [c] : ac + atp <==> actp + adp | b2296, b3115 |
| ACt6 | ac[e] + h[e]<==> ac[c] + h[c] | b4067 |
| ASNS2 | [c] : asp-L + atp + nh4 --> amp + asn-L + h + ppi | b3744 |
| CBMK2 | [c] : atp + co2 + nh4 --> adp + cdp + (2) h | b0323, b2874, b0521 |
| ENO | [c] : 2pg <==> h2o + pep | b2779 |
| FDH2 | for[c] + (3) h[c] + ubq8[c] --> co2[c] + (2) h[e] + ubq8h2[c] | b3893 + b3893 + b3894 + b4079, b1474 + b1475 + b1476 |
| FORt | for[e] <==> for[c] | b0904, b2492 |
| FTHFD | [c] : 10fthf + h2o --> for + h + thf | b1232 |
| FUM | [c] : fum + h2o <==> mal-L | b1611, b1612, b4122 |
| G5SD | [c] : glu5p + h + nadph --> glu5sa + nadp + pi | b0243 |
| G6PDHy | [c] : g6p + nadp <==> 6pgl + h + nadph | b1852 |
| GLCpts | glc-D[e] + pep[c] --> g6p[c] + pyr[c] | b2417, b1101, b2415, b2416, b2417, b1621, b2415, b2416, b1817, b1818, b1819, b2415, b2416 |
| GLCt2 | glc-D[e] + h[e] --> glc-D[c] + h[c] | b2943 |
| GLU5K | [c] : atp + glu-L --> adp + glu5p | b0242 |
| GLUDy | [c] : glu-L + h2o + nadp <==> akg + h + nadph + nh4 | b1761 |
| GLYCL | [c] : 10fthf + h2o --> for + h + thf | b1232 |
| HEX1 | [c] : atp + glc-D --> adp + g6p + h | b2388 |
| MDH | [c] : mal-L + nad <==> h + nadh + oaa | b3236 |
| ME1x | [c] : mal-L + nad --> co2 + nadh + pyr | b1479 |
| ME2 | [c] : mal-L + nadp --> co2 + nadph + pyr | b2463 |
| MTHFC | [c] : h2o + methf <==> 10fthf + h | b0529 |
| NADH6 | (4.5) h[c] + nadh[c] + ubq8[c] --> (3.5) h[e] + nad[c] + ubq8h2[c] | b2276, b2277, b2278, b2279, b2280, b2281, b2282, b2283, b2284, b2285, b2286, b2287, b2288 |
| PDH | [c] : coa + nad + pyr --> accoa + co2 + nadh | b0114, b0115, b0116 |
| PGDH | [c] : 6pgc + nadp --> co2 + nadph + ru5p-D | b2029 |
| PGI | [c] : g6p <==> f6p | b4025 |
| PGL | [c] : 6pgl + h2o --> 6pgc + h | b0767 |
| PGM | [c] : 3pg <==> 2pg | b3612 |
| PPS | [c] : atp + h2o + pyr --> amp + (2) h + pep + pi | b1702 |
| PTAr | [c] : accoa + pi <==> actp + coa | b2297, b2458 |
| RPE | [c] : ru5p-D <==> xu5p-D | b3386, b4301 |
| SUCOAS | [c] : atp + coa + succ <==> adp + pi + succoa | b0728, b0729 |
| TAL | [c] : g3p + s7p <==> e4p + f6p | b0008, b2464 |
| THD2 | (2) h[e] + nadh[c] + nadp[c] --> (2) h[c] + nad[c] + nadph[c] | b1602 + b1603 |
| THD5 | [c] : nad + nadph --> nadh + nadp | b1602 + b1603, b3962 |
| TKT1 | [c] : r5p + xu5p-D <==> g3p + s7p | b2935, b2465 |
| TKT2 | [c] : e4p + xu5p-D <==> f6p + g3p | b2935, b2465 |

TABLE 3

List of the metabolite abbreviations, the corresponding names and locations of all the metabolites that participate in the reactions listed in Supplementary Table 2.

| Metabolite Abbreviation | Compartment | Metabolite Name |
|---|---|---|
| 10fthf | Cytosol | 10-Formyltetraftydrofolate |
| 13dpg | Cytosol | 3-Phospho-D-glyceroyl phosphate |
| 2dmmq8 | Cytosol | 2-Demethylmenaquinone 8 |
| 2dmmql8 | Cytosol | 2-Demethylmenaquinol 8 |
| 2h3opp | Cytosol | 2-Hydroxy-3-oxopropanoate |
| 2pg | Cytosol | D-Glycerate 2-phosphate |
| 3pg | Cytosol | 3-Phospho-D-glycerate |
| 6pgc | Cytosol | 6-Phospho-D-gluconate |
| 6pgl | Cytosol | 6-phospho-D-glucono-1,5-lactone |
| Ac | Cytosol | Acetate |
| ac[e] | Extra-organism | Acetate |
| Accoa | Cytosol | Acetyl-CoA |
| Actp | Cytosol | Acetyl phosphate |
| Adp | Cytosol | ADP |
| Akg | Cytosol | 2-Oxoglutarate |
| asn-L | Cytosol | L-asparagine |
| asp-L | Cytosol | L-aspartate |
| Atp | Cytosol | ATP |
| Cbp | Cytosol | Carbamoyl phosphate |
| co2 | Cytosol | CO2 |
| Coa | Cytosol | Coenzyme A |
| Dha | Cytosol | Dihydroxyacetone |
| Dhap | Cytosol | Dihydroxyacetone phosphate |
| dhor-S | Cytosol | (S)-Dihydroorotate |
| e4p | Cytosol | D-Erythrose 4-phosphate |
| Etoh | Cytosol | Ethanol |
| etoh[e] | Extra-organism | Ethanol |
| f6p | Cytosol | D-Fructose 6-phosphate |
| Fad | Cytosol | FAD |
| fadh2 | Cytosol | FADH2 |
| Fdp | Cytosol | D-Fructose 1,6-bisphosphate |
| Fgam | Cytosol | N2-Formyl-N1-(5-phospho-D-ribosyl)glycinamide |
| For | Cytosol | Formate |
| for[e] | Extra-organism | Formate |
| Fum | Cytosol | Fumarate |
| fum[e] | Extra-organism | Fumarate |
| g3p | Cytosol | Glyceraldehyde 3-phosphate |
| g6p | Cytosol | D-Glucose 6-phosphate |
| Gar | Cytosol | N1-(5-Phospho-D-ribosyl)glycinamide |
| glc-D[e] | Extra-organism | D-Glucose |
| glu5p | Cytosol | L-glutamate 5-phosphate |
| glu5sa | Cytosol | L-glutamate 5-semialdehyde |
| glu-L | Cytosol | L-Glutamate |
| Glx | Cytosol | Glyoxylate |
| Gly | Cytosol | Glycine |
| glclt | Cytosol | Glycolate |
| glyclt[e] | Extra-organism | Glycolate |
| glyc-R | Cytosol | (R)-Glycerate |
| H | Cytosol | H+ |
| h[e] | Extra-organism | H+ |
| h2o | Cytosol | H2O |
| hom-L | Cytosol | L-Homoserine |
| lac-D | Cytosol | D-Lactate |
| lac-D[e] | Extra-organism | D-Lactate |
| mal-L | Cytosol | L-Malate |
| Methf | Cytosol | 5,10-Methenyltetrahydrofolate |
| Mlthf | Cytosol | 5,10-Methylenetetrahydrofolate |
| Nad | Cytosol | Nicotinamide adenine dinucleotide |
| Nadh | Cytosol | Nicotinamide adenine dinucleotide—reduced |
| Nadp | Cytosol | Nicotinamide adenine dinucleotide phosphate |
| Nadph | Cytosol | Nicotinamide adenine dinucleotide phosphate—reduced |
| nh4 | Cytosol | Ammonium |
| o2 | Cytosol | O2 |
| Oaa | Cytosol | Oxaloacetate |
| orn-L | Cytosol | L-Ornithine |
| Orot | Cytosol | Orotate |
| Pep | Cytosol | Phosphoenolpyruvate |
| Phom | Cytosol | O-Phospho-L-homoserine |
| Pi | Cytosol | Phosphate |
| pi[e] | Extra-organism | Phosphate |
| Ppa | Cytosol | Propionate |
| Ppcoa | Cytosol | Propanoyl-CoA |
| ppi | Cytosol | Diphosphate |
| Ptrc | Cytosol | Putrescine |
| Pyr | Cytosol | Pyruvate |
| pyr[e] | Extra-organism | Pyruvate |
| r5p | Cytosol | alpha-D-Ribose 5-phosphate |
| ru5p-D | Cytosol | D-Ribulose 7-phosphate |
| s7p | Cytosol | Sedoheptulose 7-phosphate |
| Succ | Cytosol | Succinate |
| succ[e] | Extra-orpnism | Succinate |
| Succoa | Cytosol | Succinyl-CoA |
| Thf | Cytosol | 5,6,7,8-Tetrahydrofolate |
| thr-L | Cytosol | L-Threonine |
| ubq8 | Cytosol | Ubiquinone-8 |
| ubq8h2 | Cytosol | Ubiquinol-8 |
| xu5p-D | Cytosol | D-Xylulose 5-phosphate |

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A non-naturally Escherichia coli comprising a set of metabolic modifications obligatorily coupling fumaric acid production to growth of said Escherichia coli, said set of metabolic modifications comprising disruption of at least one gene encoding an enzyme catalyzing reactions selected from the group consisting of:
   (1) Fumarase (FUM), Phosphogluconate dehydrogenase (PGDH), Formyltetrahydrofolate hydrolase (FTHFD) and
   (2) Fumarase (FUM), Phosphogluconate dehydrogenase (PGDH), Serine hydroxymethyl transferase (GHMT2) or an ortholog thereof, which confer stable growth-coupled production of fumaric acid.

2. A fumarate dialkyl ester production system, comprising:
   (a) a vessel comprising a culture of a non-naturally Escherichia coli in nutrients and media, said non-naturally occurring Escherichia coli comprising a set of metabolic modifications obligatorily coupling fumaric acid production to growth of said microbial organism, said set of metabolic modifications comprising disruption of at least one gene encoding an enzyme catalyzing reactions selected from the group consisting of:
   (1) Fumarase (FUM), Phosphogluconate dehydrogenase (PGDH), Formyltetrahydrofolate hydrolase (FTHFD) and
   (2) Fumarase (FUM), Phosphogluconate dehydrogenase (PGDH), Serine hydroxymethyl transferase (GHMT2) or an ortholog thereof, which confer stable growth-coupled production of fumaric acid; and (b) a source of at least one diesterification reagent and in communication with the vessel wherein the at least one diesterification reagent is sufficient to produce fumarate dialkyl ester from said fumaric acid.

3. The production system of claim 2, wherein said reactions encoding said metabolic modifications further comprises disruption of at least one gene selected from a set encoding enzyme reactions selected from the group consisting of reactions:
  (1) Fumarase (FUM), Phosphogluconate dehydrogenase (PGDH), Formyltetrahydrofolate hydrolase (FTHFD), Acetate kinase (ACKr)
  (2) Fumarase (FUM), Phosphogluconate dehydrogenase (PGDH), Formyltetrahydrofolate hydrolase (FTHFD), Glutamate dehydrogenase (GLUDy);
  (3) Fumarase (FUM), Phosphogluconate dehydrogenase (PGDH), Formyltetrahydrofolate hydrolase (FTHFD), Transhydrogenase (THD2); and
  (4) Fumarase (FUM), Formyltetrahydrofolate hydrolase (FTHFD), Transhydrogenase (THD2), Acetate kinase (ACKr), Phosphoglyceromutase (PGM), Phosphogluconal acotonase (PGL).

4. The production system of claim 2, wherein said disruption comprises a deletion of at least one gene within said reaction set.

5. The production system of claim 2, wherein said diesterification reagent is an alcohol at a 1:2 molar ratio of fumaric acid produced in culture with the alcohol under condensation reaction conditions sufficient to produce fumarate dialkyl ester and water at a 1:2 molar ratio.

6. The production system of claim 5, further comprising an esterification catalyst.

7. The production system of claim 6, wherein said esterification catalyst is sulfuric acid ($H_2SO_4$) or p-toluene sulfonic acid.

8. The fumarate dialkyl ester production system of claim 2, 5 or 7, wherein the fumarate dialkyl ester is dibutyl fumarate.

9. The production system of claim 2, wherein said nutrients and media comprise at least one carbon substrate selected from glucose, xylose, arabinose, galactose, mannose or fructose.

10. A process for producing an olefin, comprising: (a) culturing by fermentation in a sufficient amount of nutrients and media a microbial organism that produces a first olefin, and (b) contacting said first olefin with a sufficient amount of a disubstituted alkene in the presence of an olefin metathesis transformation catalyst to produce second, different olefin; wherein the first olefin is fumaric acid, the disubstituted alkene is 2-butene, and the second, different olefin is crotonic acid and the microbial organism that produces the first olefin is a non-naturally occurring *Escherichia coli* organism comprising a set of metabolic modifications obligatorily coupling fumaric acid production to growth of said *Escherichia coli* to produce fumaric acid, wherein said set of metabolic modifications comprises disruption of at least one gene encoding an enzyme catalyzing reactions selected from the group of consisting of:
  (1) Fumarase (FUM), Phosphogluconate dehydrogenase (PGDH), Formyltetrahydrofolate hydrolase (FTHFD) and
  (2) Fumarase (FUM), Phosphogluconate dehydrogenase (PGDH), Serine hydroxymethyl transferase (GHMT2) or an ortholog thereof, which confer stable growth-coupled production of fumaric acid.

11. A process for producing dibutyl fumarate comprising: (a) culturing in a sufficient amount of nutrients and media a non-naturally occurring *Escherichia coli* organism comprising a set of metabolic modifications obligatorily coupling fumaric acid production to growth of said *Escherichia coli* to produce fumaric acid; and (b) performing diesterification of said fumaric acid to produce dibutyl fumarate, wherein said set of metabolic modifications comprises disruption of at least one gene encoding an enzyme catalyzing reactions selected from the group consisting of:
  (1) Fumarase (FUM), Phosphogluconate dehydrogenase (PGDH), Formyltetrahydrofolate hydrolase (FTHFD) and
  (2) Fumarase (FUM), Phosphogluconate dehydrogenase (PGDH), Serine hydroxymethyl transferase (GHMT2) or an ortholog thereof, which confer stable growth-coupled production of fumaric acid; and
  (b) at least one diesterification reagent sufficient to produce fumarate dialkyl ester from said fumaric acid.

12. The process of claim 11, wherein performing diesterification comprises contacting said fumaric acid with an alcohol at a 1:2 molar ratio in under condensation reaction conditions sufficient to produce dibutyl fumarate and water at a 1:2 molar ratio.

13. The process of claim 11, wherein performing diesterification comprises contacting said fumaric acid with a butyl alcohol and sulfuric acid —($H_2SO_4$)— or p-toluene sulfonic acid.

14. A process comprising a) culturing by fermentation in a sufficient amount of nutrients and media a non-naturally occurring *Escherichia coli* that produces fumaric acid; b) esterification of said fumaric acid to provide fumarate dibutyl ester; and c) olefin metathesis of said fumarate dibutyl ester to butyl acrylate in the presence of metathesis ruthenium catalyst bearing an N-heterocyclic carbene ligand, wherein said non-naturally occurring *Escherichia coli* comprises a set of metabolic modifications comprising disruption of at least one gene encoding an enzyme catalyzing reactions selected from the group consisting of:
  (1) Fumarase (FUM), Phosphogluconate dehydrogenase (PGDH), Formyltetrahydrofolate hydrolase (FTHFD) and
  (2) Fumarase (FUM), Phosphogluconate dehydrogenase (PGDH), Serine hydroxymethyl transferase (GHMT2) or an ortholog thereof, which confer stable growth-coupled production of fumaric acid.

15. The method of claim 14, wherein the metathesis ruthenium catalyst bearing an N-hetrocyclic carbine ligand is selected from the group consisting of
  [1,3 bis(2,4,6-trimethylphenyl)-2-imidazolidinylidene] dichloro[(2-(1-methyleth-oxy)phenyl)methylene]ruthenium;
  [1,3-bis(2-methylphenyl)-2-imidazolidinylidene]dichloro (benzylidene) (tricyclohexylphosphine)ruthenium(II);
  [1,3-bis(2,4,6-trimethylphenyl)-2-imidazolidinylidene] dichloro(3-methyl-2-butenylidene)(tricyclohexylphosphine)ruthenium(II); and
  [1,3-bis-(2,4,6 trimethylphenyl)-2-imidazolidinylidene] dichloro(phenylmethylene)(tricyclo- hexylphosphine) ruthenium.

* * * * *